United States Patent
Seong et al.

(10) Patent No.: US 9,579,398 B2
(45) Date of Patent: Feb. 28, 2017

(54) PHARMACEUTICAL USE OF FAM19A5 INVOLVED IN REGULATING GLIOGENESIS

(71) Applicant: Neuracle Science Co., Ltd., Seoul (KR)

(72) Inventors: Jae Young Seong, Seoul (KR); Jong Ik Hwang, Seoul (KR); Woong Sun, Seoul (KR); Eun Bee Cho, Seoul (KR); Won-ki Kim, Seoul (KR)

(73) Assignee: Neuracle Science Co., Ltd., Seoul (KR)

( * ) Notice: Subject to any disclaimer, the term of this patent is extended or adjusted under 35 U.S.C. 154(b) by 0 days.

(21) Appl. No.: 14/378,505

(22) PCT Filed: Feb. 15, 2013

(86) PCT No.: PCT/KR2013/001179
§ 371 (c)(1),
(2) Date: Aug. 13, 2014

(87) PCT Pub. No.: WO2013/122408
PCT Pub. Date: Aug. 22, 2013

(65) Prior Publication Data
US 2015/0118230 A1    Apr. 30, 2015

(30) Foreign Application Priority Data

Feb. 15, 2012  (KR) .................. 10-2012-0015177
Feb. 15, 2013  (KR) .................. 10-2013-0016094

(51) Int. Cl.
| | | |
|---|---|---|
| A61K 39/395 | (2006.01) |
| A61P 25/00 | (2006.01) |
| A61K 48/00 | (2006.01) |
| A61K 38/17 | (2006.01) |
| C07K 16/18 | (2006.01) |
| C12N 15/113 | (2010.01) |
| C07K 14/47 | (2006.01) |
| C07K 16/24 | (2006.01) |
| C12Q 1/68 | (2006.01) |
| A61K 39/00 | (2006.01) |

(52) U.S. Cl.
CPC .......... *A61K 48/00* (2013.01); *A61K 38/1709* (2013.01); *C07K 14/4701* (2013.01); *C07K 14/4702* (2013.01); *C07K 16/18* (2013.01); *C07K 16/24* (2013.01); *C12N 15/113* (2013.01); *C12Q 1/6886* (2013.01); *A61K 2039/505* (2013.01); *C07K 2317/31* (2013.01); *C07K 2317/54* (2013.01); *C07K 2317/55* (2013.01); *C07K 2317/76* (2013.01); *C12N 2310/11* (2013.01); *C12N 2310/141* (2013.01); *C12Q 2600/156* (2013.01)

(58) Field of Classification Search
None
See application file for complete search history.

(56) References Cited

U.S. PATENT DOCUMENTS

2009/0221670 A1*  9/2009  Borglum .............. C12Q 1/6883
                                                      514/44 A
2010/0233081 A1    9/2010  Warren et al.

FOREIGN PATENT DOCUMENTS

KR    1020100020445    1/2012

OTHER PUBLICATIONS

Robel et al., Nature, vol. 12: 88-104, Feb. 2011.*
Dehay and Kennedy, "Cell-cycle control and cortical development", Nature Reviews Neuroscience, 8:438-450 (2007).
Molyneaux et al., "Neuronal subtype specification in the cerebral cortex", Nature Reviews Neuroscience, 8:427-437 (2007).
Angevine and Sidman, "Autoradiographic study of cell migration during histogenesis of cerebral cortex in the mouse", Nature, 192:766-768 (1961).
Caviness et al., Proliferative events in the cerebral ventricular zone, Brain & Development, 17:159-63 (1995).
Bayer et al., "Cell migration in the rat embryonic neocortex" J. Comp. Neurol., 307:499-516 (1991).
Miller et al., "Timing is everything: Making neurons versus glia in the developing cortex", Neuron, 54:357-369 (2007).
Doetsch, "A niche for adult neural stem cells", Curr. Opin. Genet. Dev., 13:543-550 (2003).
Doetsch et al., "Subventricular zone astrocytes are neural stem cells in the adult mammalian brian", Cell, 97:703-716, (1999).
Lois and Alvarez, "Proliferating subventricular zone cells in the adult mammalian forebrain can differentiate into neurons and glia", Proc. Natl. Acad. Sci., 90:2074-2077 (1993).
Palmer, "The adult rat hippocampus contains primordial neural stem cells", Mol. Cell. Neurosci. 8:389-404 (1997).
Temple, "The development of neural stem cells", Nature, 414:112-117 (2001).
Nedergaard et al., "New roles for astrocytes: redefining the functional architecture of the brain", Trends Neurosci., 26:523-530 (2003).
Ullian et al., "Control of synapse number By glia", Science, 291:657-661 (2001).
Song et al., "Astroglia induce neurogenesis from adult neural stem cells" Nature, 417:39-44 (2002).
Temple et al., "Isolated rat cortical progenitor cells are maintained in division in vitro by membrane-associate factors", Development, 120:999-1008 (1994).

(Continued)

*Primary Examiner* — Kimberly A. Ballard
*Assistant Examiner* — Stacey N MacFarlane
(74) *Attorney, Agent, or Firm* — Sterne, Kessler, Goldstein & Fox P.L.L.C.

(57) ABSTRACT

The present invention relates to the pharmaceutical use of FAM19A5 involved in regulating gliogenesis, and more specifically, to the use of FAM19A5 in the prevention, diagnosis, or treatment of central nervous system injuries, degenerative brain diseases, or central nervous system diseases, FAM19A5 being spread in the neural stem cells in vertebrates and regulating gliogenesis.

24 Claims, 15 Drawing Sheets

(56) References Cited

OTHER PUBLICATIONS

Seri et al., "Astrocytes give rise to new neurons in the adult mammalian hippocampus", J. Neurosci., 21:7153-7160 (2001).
Svendsen, "The amazing astrocyte", Nature, 417:29-32 (2002).
Myer et al., "Essential protective roles of reactive astrocytes in traumatic brain injury", Brain, 129:2761-2772 (2006).
Chen and Swanson, "Astrocytes and bran injury", J. Cereb. Blood Flow Metab., 23:137-149 (2003).
Cunnigham et al., "Physiological thresholds for irreversible tissue damage in contusional regions following traumatic brain injury", Brain, 128:1931-1942 (2005).
Faden, "Neuroprotection and traumatic brain injury: theoretical option or realistic proposition", Curr. Opin, Neurol., 15:707-712 (2002).
Katayama et al., "Massive increases in extracellular potassium and the indiscriminate release of glutamate following concussive brain injury", J. Neurosurg., 73:889-900 (1990).
Faideau et al., "In vivo expression of polyglutamine-expanded huntingtin by mouse striatal astrocytes impairs glutamate transport: a correlation with huntington's disease subjects", Hum. Mol. Genet., 19, 15, 3053-3067 (2010).
Chen et al., "EphA2 receptor tyrosine kinase as a promosing target for cancer therapeutics", 5:149-157 (2005).
Rodriguez et al., "Astroglia in dementia and Alzheimer's disease", Cell Death Differ., 16:378-385 (2009).
Robel et al., "Genetic deletion of Cdc42 reveals a crucial role for astrocyte recruitment to the injury site in vitro and in vivo", J. Neurosci., 31(35):12471-12482 (2011).

Talbott et al., "Endogenous Nkx2.2+/Olig2+ oligodendrocyte precursor cells fail to remyelinate the demyelinated adult rat spinal cord in the absense of astrocytes", Exp. Neurol., 192:11-24 (2005).
Shimada et al., "Self-renewal and differentiation of reactive astrocyte-derived neural stem/progenitor cells isolated from the cortical peri-infarct area after stroke", 32(33):7926-2940 (2012).
Sofroniew and Vinters, "Astrocytes: biology and pathology" Acta Neuropathol., 119:7-35 (2010).
Lister et al., "Hotspots of aberrant epigenomic reprogramming in human induced pluripotent stem cells" Nature, 471: 68-76 (2011).
Yilmaz et al., "Induction of neuro-protective/regenerative genes in stem cells infiltrating post-ischemic brain tissue", Experimental & Translational Stroke Med. 2:11 (2011).
Teresita Diaz De Stahl et al., "Chromosome 22 Tiling-Path Array—CGH Analysis Identifies Germ-Line and Tumor-Specific Aberrations in Patients with Glioblastoma Multiforme." Genes Chromosomes & Cancer (2005) 44;161-169.
Y. Tom Tang et al., "TAFA: a novel secreted family with conserved cysteine residues and restricted expression in the brain." Genomics (2004) 83; 727-734.
Sarah Juel Paulsen et al., "The putative neuropeptide TAFA5 is expressed in the hypothalamic paraventricular nucleus and is regulated by dehydration." Brain Research (2008) 1199; 1-9.
Extended European Search Report for Application No. 13748791.4, mailed Jul. 22, 2015, six (6) pages.
International Search Report and Written Opinion for International Application No. PCT/KR2013/001179, mailed May 31, 2013, eleven (11) pages.

* cited by examiner

Fig. 4
(A) Western blotting
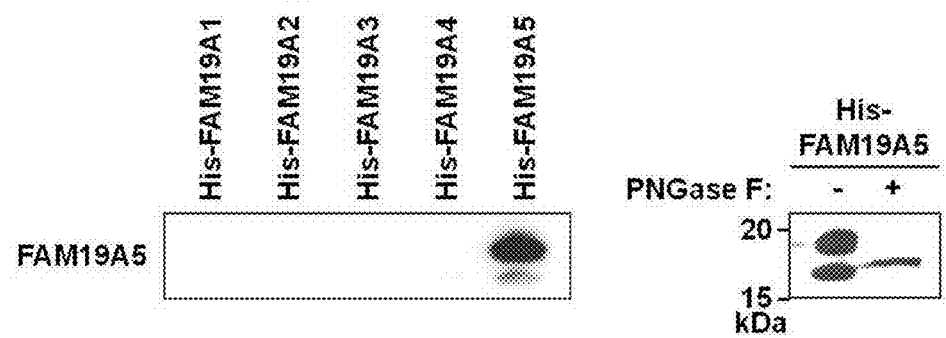
(B) Immunocytochemistry
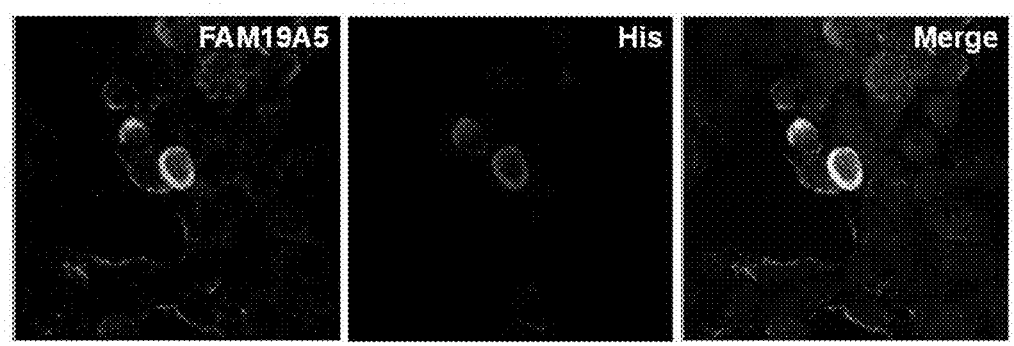

Fig. 7

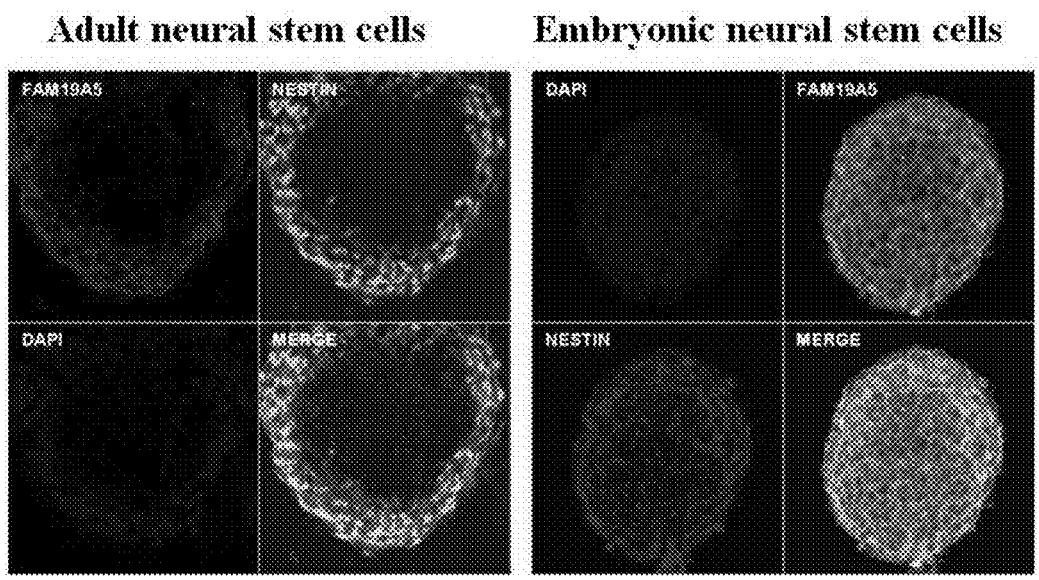

Fig. 8

(A) Immunocytochemistry

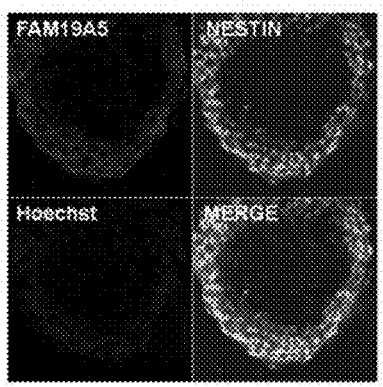

(B) RT-PCR

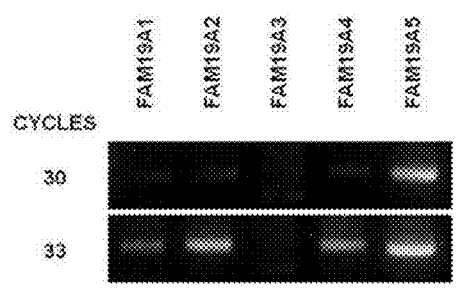

(C) Microarray

FAM19A5 family genes in the SVZ region of the adult mouse

| Gene symbol | Gene name | Accession number | Raw | Normalized |
|---|---|---|---|---|
| FAM19A1 | family with sequence similarity 19, member A1 | BC132179 | 61.89188 | 5.9299307 |
| FAM19A2 | family with sequence similarity 19, member A2 | BC027082 | 196.82034 | 7.6002617 |
| FAM19A3 | family with sequence similarity 19, member A3 | BC118531 | 74.83356 | 6.2145233 |
| FAM19A4 | family with sequence similarity 19, member A4 | BC089490 | 94.36983 | 6.5479784 |
| FAM19A5 | family with sequence similarity 19, member A5 | BC015306 | 1155.4615 | 10.16699 |

Fig. 13
(A) Immunohistochemistry
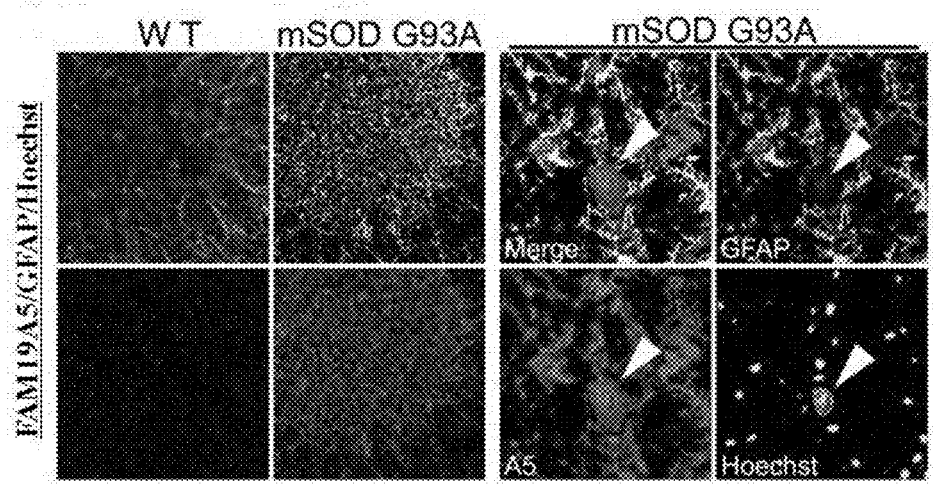
(C) RIA(FAM19A5 in blood)
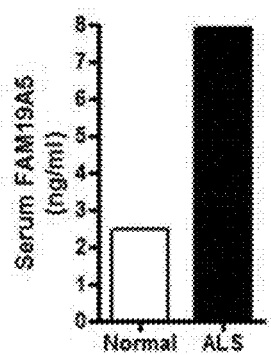
(B) Western blotting

Fig. 14
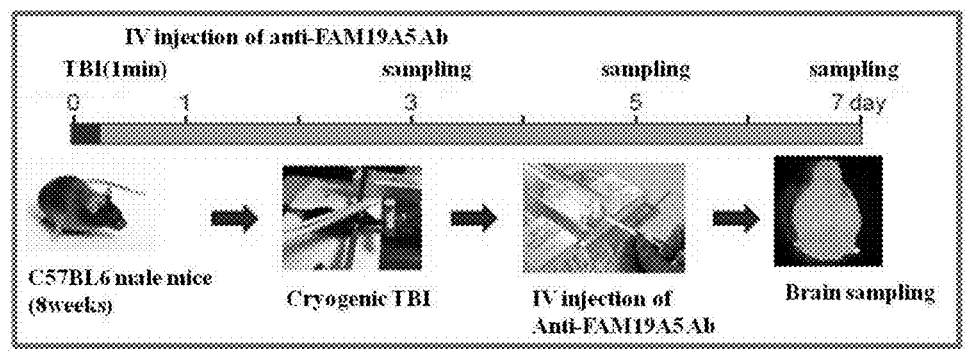
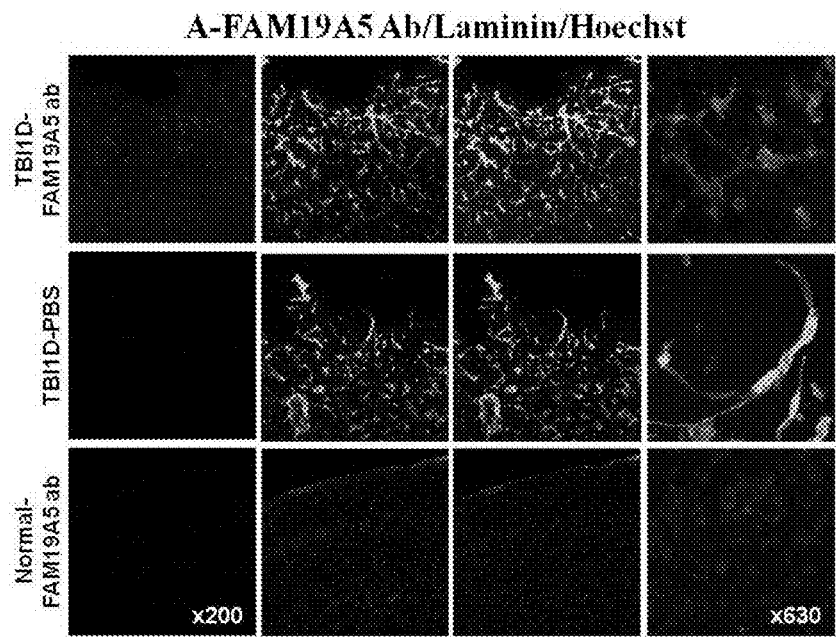

PHARMACEUTICAL USE OF FAM19A5 INVOLVED IN REGULATING GLIOGENESIS

This application is a national stage application, filed under 35 U.S.C. §371, of International Application No. PCT/KR2013/001179, filed on Feb. 15, 2013, which claims priority from Korean Patent Application Nos. 10-2012-0015177, filed on Feb. 15, 2012 and 10-2013-0016094, filed on Feb. 15, 2013, the contents of which are herein incorporated by reference in their entireties.

INCORPORATION-BY-REFERENCE OF SEQUENCE LISTING

The contents of the text file named "G14U13C0343P_US_SL_ST25.txt", which was created on Dec. 23, 2014, and is 12 kilobytes in size, are hereby incorporated by reference in their entirety.

BACKGROUND

1. Field of the Invention

The present invention relates to a pharmaceutical use of FAM19A5 regulating proliferation and differentiation of neural stem cells in vertebrates for diagnosing, preventing, or treating damage to the central nervous system, degenerative brain diseases, or central nervous system diseases.

2. Discussion of Related Art

A neural plate becomes a neural tube during early development, and a cavity within neural tube forms a ventricle through the developmental process. The cell layer closest to the ventricle is the ventricular zone. An additional proliferating cell layer is formed above the ventricular zone through a neurogenesis process, which is referred to as the subventricular zone. Progenitor cells in the ventricular zone and the subventricular zone have properties of neural stem cells and migrate to a cortical plate through a complex control system [Dehay and Kennedy, *Nat Rev Neurosci* 8:438-450, 2007; Molyneaux et al., *Nat Rev Neurosci* 8:427-437, 2007; Angevine and Sidman, *Nature* 192:766-768, 1961; Caviness and Takahashi, *Brain Dev* 17:159-163, 1995].

Neural stem cells have an ability to divide continuously, that is, a self-renewal ability, and differentiate into neurons, astrocytes, and oligodendrocytes of the central nervous system. The differentiation process into neurons mainly occurs during the embryonic period, but the differentiation process into glial cells occurs after birth [Bayer et al., *J Comp Neurol* 307:499-516, 1991; Miller and Gauthier, *Neuron* 54:357-369, 2007].

Differentiation from neural stem cells into neurons and glial cells is a phenomenon that is continuously observed in developmental process of the brain and an adult's brain. In the adult brain, neurogenesis occurs in two different brain regions, the subventricular zone of the lateral ventricle and the dentate gyms of the hippocampus. In the subventricular zone, ependymal cells closest to the ventricle and astrocytes distributed therealong serve as neural stem cells, and the two types of cells become neuroblasts through transient amplifying cells [Doetsch, *Curr Opin Genet Dev* 13:543-550, 2003; Doetsch et al., *Cell* 97:703-716, 1999; Lois and Alvarez-Buylla, *Proc. Natl. Acad. Sci. USA* 90:2074-2077, 1993; Palmer et al., *Mol Cell Neurosci* 8:389-404, 1997; Temple, *Nature* 414:112-117, 2001].

In order to maintain normal functions of the brain, a numerical balance of neurons and glial cells is essential. In the past, astrocytes, which accounted for the majority of glial cells, were regarded as merely protective cells that aided neurons in performing their functions. On the contrary, astrocytes are now known to affect the environment around neurons beyond serving as a structural support. That is, astrocytes secrete growth factors, regulate functions of neurons, and help maintain the barrier between blood vessels and the brain. Also, astrocytes are known to play a more active role by directly regulating structure formation and synapse function between neurons [Nedergaard et al., *Trends Neurosci* 26:523-530, 2003; Ullian et al., *Science* 291:657-661, 2001; Song et al., *Nature* 417:39-44, 2002; Temple and Davis, *Development* 120:999-1008, 1994; Seri et al., *J Neurosci* 21:7153-7160, 2001; Svendsen, *Nature* 417:29-32, 2002].

Functional significance of astrocytes is pathologically known through a great deal of research. When the brain is damaged, astrocytes actively proliferate, become reactive, and hypertrophy is observed. Active proliferation of such glial cells is advantageous in that it promotes recovery of tissues shortly after initial damage and prevents damage from spreading. However, when such a phenomenon is repeated, regeneration of neurons is suppressed and an inflammatory response is caused, and damage is applied, which may result in degenerative brain disease [Myer et al., *Brain* 129:2761-2772, 2006; Chen and Swanson, *J Cereb Blood Flow Metab* 23:137-149, 2003; Cunningham et al., *Brian* 128: 1931-1942, 2005; Faden, *Curr Opin Neurol* 15:707-712, 2002; Katayama et al., *J Neurosurg* 73:889-900, 1990].

Gliosis is a phenomenon that commonly occurs in various pathological processes of the central nervous system and is caused by hyperproliferation and activation of astrocytes resulting from neuronal damage. When damage is applied to the central nervous system, normal astrocytes become hypertrophic, reactive astrocytes that increase generation of an intermediate filament protein called glial fibrillary acidic protein (GFAP). Various glial cells including reactive astrocytes undergo hyperproliferation after damage and a solid cell layer named a glial scar that is a product of the healing process is formed. Such gliosis is observed in degenerative brain diseases including Huntington's disease, Parkinson's disease, and Alzheimer's disease, in cerebrospinal damage, and various pathological phenomena of the central nervous system such as strokes and brain tumors [Faideau et al., *Hum Mol Genet*, 2010; Chen et al., *Curr Drug Targets*, 2005; Rodriguez et al., *Cell Death Differ*, 2009; Robel et al., *J Neurosci*, 2011; Talbott et al., *Exp Neurol*, 2005; Shimada et al., *J Neurosci;* 2012; Sofroniew and Vinters, *Acta Neuropathol*, 2010]

In general, gliosis has various influences depending on the circumstances in which damage has initially occurred or the time that has elapsed after a wound has occurred. After damage, initial reactive astrocytes secrete nerve growth factors preventing programmed cell death such as GDNF and cause resumption in the uptake of glutamic acid, thereby protecting neurons. In addition, the initial reactive astrocytes positively function in processes such as recovery of the blood-brain barrier, isolating a region in which damage has occurred, and preventing infection of healthy tissues. However, when a predetermined time elapses after damage, glia scars are formed by hyperproliferated reactive astrocytes and surround a damaged region like a net, and an inhibitory extracellular matrix accumulates. A dense structure of such proteins serves as a barrier that prevents neurons from being physically and chemically regenerated and reconstructing connections. Also, substances that induce inflammation and neurotoxic substances such as cytotoxic cytokines are secreted to induce apoptosis of neurons, inhibit functional recovery, and worsen pathological symptoms. In the related art, central nervous system diseases may be detected through a histopathological test, computerized tomography (CT), or magnetic resonance imaging (MRI). However, diagnosis using such methods may be possible only after the disease has progressed to some extent. Therefore, development of a diagnosis marker that may rapidly and accurately identify the degree of progress of central nervous system disease is essential. Also, a method of treatment in which neurons survive at the early stage of damage and generation of glia scars is minimized and neuron regeneration is promoted at the later phase will be the best method.

SUMMARY OF THE INVENTION

The present invention is directed to providing a pharmaceutical use of FAM19A5 for diagnosing, preventing, or treating central nervous system damage, degenerative brain diseases, or central nervous system diseases by identifying a role of FAM19A5 in regulating gliogenesis.

To solve the above-described objects, the present invention provides a composition for regulating proliferation or differentiation of stem cells containing FAM19A5 (family with sequence similarity 19, member A5) or an inhibitor thereof as a proliferation or differentiation regulator.

The present invention also provides a composition for diagnosing central nervous system damage, degenerative brain diseases, or central nervous system diseases, containing an agent for measuring mRNA of FAM19A5 (family with sequence similarity 19, member A5) genes or a protein level thereof.

The present invention also provides a composition for treating early traumatic brain injury, containing FAM19A5 (family with sequence similarity 19, member A5).

The present invention also provides a use of FAM19A5 for preparing a pharmaceutical composition for treating early traumatic brain injury.

The present invention also provides a method for treating early traumatic brain injury in animals, including administering a composition for treating early traumatic brain injury, containing a pharmaceutically effective dose of FAM19A5 to a subject.

The present invention also provides a composition for preventing or treating degenerative brain diseases or central nervous system diseases, containing an FAM19A5 (family with sequence similarity 19, member A5) inhibitor.

The present invention also provides a use of the FAM19A5 inhibitor for preparing a pharmaceutical composition for preventing or treating degenerative brain diseases or central nervous system diseases.

The present invention also provides a method of treating degenerative brain diseases or central nervous system diseases in animals, including administering a composition for preventing or treating degenerative brain diseases or central nervous system diseases, containing a pharmaceutically effective dose of the FAM19A5 inhibitor to a subject.

The present invention also provides a method of screening for preventive or therapeutic medicine for brain diseases or central nervous system diseases, including:
contacting FAM19A5 (family with sequence similarity 19, member A5) genes with a candidate material in vitro, and
determining whether the candidate material promotes or inhibits expression of the genes.

The present invention also provides a method of screening for a preventive or therapeutic medicine for brain diseases or central nervous system diseases, including:
contacting FAM19A5 (family with sequence similarity 19, member A5) proteins with a candidate material in vitro, and
determining whether the candidate material promotes or inhibits a function or an activity of the protein.

BRIEF DESCRIPTION OF THE DRAWINGS

FIG. 4 shows the results obtained by determining the binding specificity of FAM19A5-specific antibody and His-FAM19A5 proteins using Western blotting (A) and immunocytochemistry (B).

FIG. 7 shows the results obtained by measuring expression of FAM19A5 peptides in neurospheres developing in neural stem cells of mouse, using immunocytochemistry.

FIG. 8 shows the results obtained by measuring expression of FAM19A5 in neurospheres. (A) shows the results obtained through immunocytochemistry, (B) shows the results obtained through RT-PCR, and (C) shows the results obtained through a microarray.

FIG. 13 shows the results obtained by measuring changes in FAM19A5 proteins in an amyotrophic lateral sclerosis model using immunohistochemistry (A), Western blotting (B), and radioimmunoassay (C).

FIG. 14 shows the fluorescence signal in brain tissues when treated with FAM19A5-specific antibodies after traumatic brain injury.

DETAILED DESCRIPTION OF EXEMPLARY EMBODIMENTS

Figure 1:
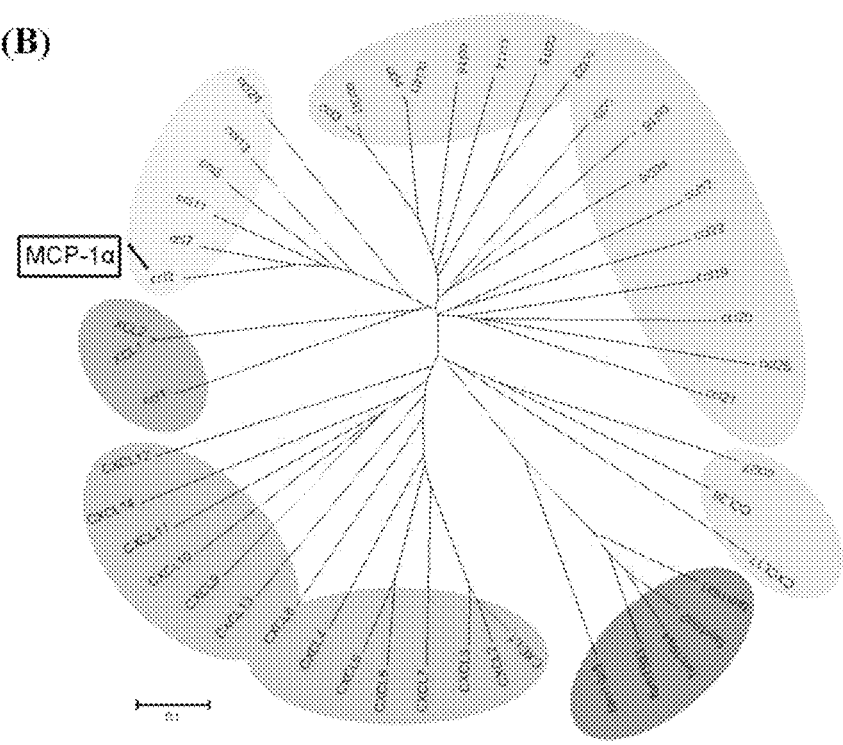
FIG. 1 shows amino acid sequences (A) of FAM19A5 peptides expressed from FAM19A5 genes of various vertebrates and a phylogenetic tree (B).

Unless particularly defined otherwise, all terms including technical and scientific terms used herein have the same meaning as commonly understood by one of ordinary skill in the art to which this invention belongs. In general, the nomenclatures used in this specification and the experimental methods described below are widely known and generally used in the related art.

FAM19A5 (family with sequence similarity 19, member A5) is a member of FAM19A family genes composed of five highly homologous genes that encode small secretory proteins. These proteins contain conserved cysteine residues at fixed positions, and are related to MIP-1 alpha which is a member of the CC-chemokine gene family. It is known that these proteins are predominantly expressed mainly in the brain and the spinal cord, generated and secreted in neurogenesis processes and by adult neural stem cells, and serve as a differentiation regulating factor for promoting generation of astrocytes.

The inventors found the presence of FAM19A5 in the body through a bioinformatics approach and by using in situ hybridization and immunohistochemistry, identified a role of FAM19A5 in a process of generating cells differentiated from neural stem cells using immunocytochemistry, and determined a therapeutic use regarding several diseases related to neurons and gliogenesis in vertebrates, and have completed the present invention.

Therefore, the present invention provides a composition for regulating proliferation or differentiation of stem cells, containing FAM19A5 (family with sequence similarity 19, member A5) as a proliferation or differentiation regulator.

According to a detailed example of the present invention, FAM19A5 is predominantly expressed in the brain of vertebrates, and particularly, strongly distributed in the ventricular zone and spinal cord region, highly expressed in the ventricular zone and the subventricular zone of even fetus in pregnancy before birth, but weakly expressed in the cortical plate at which differentiated neurons are positioned. Therefore, the present invention has demonstrated for the first time that FAM19A5 genes are strongly expressed in two regions of the central nervous system known to have a population of neural stem cells, important in formation of a complete central nervous system, and involved in generation of neurons and glial cells constituting the central nervous system.

Based on these results, expression of FAM19A5 in neurospheres developed from neural stem cells has been observed. As a result, it can be shown that FAM19A5 is distributed much more in neurospheres than other types of FAM19A family genes. This suggests that FAM19A5 may be an important peptide in the functions of adult and embryonic neural stem cells and in the differentiation process into different types of cells generated therefrom.

Through these results, it has been determined that FAM19A5 is generated and secreted from neural stem cells, that it influences generation of cells (that is, neurons or astrocytes), and their differentiation. As a result, it can be seen that FAM19A5 promotes generation of astrocytes.

Therefore, FAM19A5 may regulate the number of neurons or astrocytes differentiated from neural stem cells through a quantitative change in their number. That is, since the number of differentiated astrocytes increases through a quantitative increase in FAM19A5 and the number of differentiated neurons increases through a quantitative reduction in FAM19A5, it can be seen that FAM19A5 is a differentiation regulating factor.

In addition, according to another detailed example of the present invention, it has been determined that proliferation of neural stem cells decreases through a quantitative increase in FAM19A5 and proliferation of neural stem cells increases through a quantitative reduction in FAM19A5. Therefore, it can be seen that FAM19A5 is a proliferation regulating factor of stem cells.

Therefore, FAM19A5 or an inhibitor thereof may be used as a proliferation or differentiation regulator of stem cells.

FAM19A5 of the present invention is a secretory protein secreted from neural stem cells, it includes gene sequences encoding a typical signal peptide of an amino-terminus as a signal that can be extracellularly secreted, and has amino acid sequences of mature FAM19A5, subsequently (refer to FIG. 1).

A composition for regulating proliferation or differentiation of stem cells of the present invention may include natural or recombinant FAM19A5, FAM19A5 proteins having substantial physiological activity thereto, transgenic neural stem cells overexpressing the natural or recombinant FAM19A5, or an FAM19A5 inhibitor. The protein having substantially equivalent physiological activity includes natural/recombinant FAM19A5, a functional equivalent thereof, and a functional derivative.

The term "functional equivalent" refers to an amino acid sequence variant in which some or all of amino acids of the natural protein are substituted or some amino acids are deleted or added, and that has substantially equivalent physiological activity to that of natural FAM19A5.

The term "functional derivative" refers to a protein that has been modified to increase or decrease physical and chemical properties of the FAM19A5 protein and has substantially equivalent physiological activity to that of natural FAM19A5.

The FAM19A5 protein of the present invention originates mostly from mammals, such as, humans, mice, rats, and the like; zebra finches, chickens, zebra danios, frogs, sticklebacks, and the like, and refers to a protein having a known sequence, for example, human-derived GenBank accession no. NM_134096, NM_001191991.

According to a detailed example, FAM19A5 used in the present invention may be prepared by a genetic engineering method that is known to those skilled in the art from GenBank accession no. NM_134096, NM_001191991, and the like.

When a protein is prepared by a gene recombinant method to obtain natural FAM19A5, if mammal cells are used instead of *E. coli* or insect cells, it is considered to be more similar to the natural type in terms of the degree of activity or solubility of the protein.

The recombinant FAM19A5 protein may be isolated using a typical column chromatography method. The degree of purification of the protein may be determined by sodium dodecyl sulfate-polyacrylamide gel electrophoresis (SDS-PAGE).

The transgenic neural stem cells overexpressing the natural or recombinant FAM19A5 may be prepared by introducing a vector expressing natural or recombinant FAM19A5 into neural stem cells through a known method.

The FAM19A5 inhibitor may be any one of an antisense-oligonucleotide, siRNA, shRNA, miRNA or a vector including the same, or antibodies.

The composition for regulating proliferation or differentiation of stem cells of the present invention may be added as a proliferation or differentiation regulating factor when neural stem cells are cultured in vitro. For example, in a proliferation or differentiation-inducing culture of neural stem cells, natural or recombinant FAM19A5 or an inhibitor thereof is added such that an increase or decrease of stem cell proliferation may be regulated through a quantitative change thereof or the number of neurons or astrocytes may be regulated.

In addition, when neural stem cells and transgenic neural stem cells overexpressing natural or recombinant FAM19A5 are co-cultured to induce differentiation, the number of astrocytes may increase due to increases in amounts of FAM19A5 proteins secreted from transgenic and regular neural stem cells.

The composition for regulating proliferation or differentiation of stem cells of the present invention may further include a known differentiation-inducing factor that induces differentiation of neural stem cells in addition to FAM19A5. For example, a ciliary neurotrophic factor (CNTF), bone morphogenetic proteins (BMPs), a transforming growth factor (TGFα), or a neuregulin-1 (Nrg1)/glial growth factor-2 (GGF2) may be used.

The present invention also provides a composition for diagnosing central nervous system damage, degenerative brain diseases, or central nervous system diseases, containing an agent for measuring mRNA expression or protein concentration of FAM19A5 (family with sequence similarity 19, member A5).

When the brain is damaged, mature astrocytes actively proliferate, change to reactive astrocytes, become hypertrophic, induce rapid recovery of tissues, and prevent damage from spreading.

According to a detailed example of the present invention, FAM19A5 expression significantly increases in a damaged region, radial glial cells in the damaged region express nestin, serving as a marker and simultaneously express FAM19A5, and significantly numerically increase compared to an undamaged control group. In addition, neuroblasts migrating to a brain injury region from the subventricular zone through the corpus collosum express little or no FAM19A5. In addition to the damaged region, the number of cells expressing FAM19A5 proteins increases in a periphery region of the subventricular zone in which a neural stem cell population is positioned, and these simultaneously express GFAP serving as a marker of astrocytes.

In addition, FAM19A5 may leak into blood while the blood-brain barrier is damaged after a brain injury. The presence of FAM19A5 can be determined by a blood test. The amount of such expression tends to continuously increase over time after brain injury.

According to another detailed example of the present invention, a quantitative change in FAM19A5 protein concentration is measured in amyotrophic lateral sclerosis which is a spinal cord damage disease model. As a result, it was determined that the amount of expression increased compared to a normal model.

Therefore, FAM19A5 may be used as a biomarker for diagnosing central nervous system damage.

Also, according to another detailed example of the present invention, when FAM19A5-specific antibodies are used to treat reactive astrocytes generated due to traumatic brain injury, excessive proliferation of those astrocytes is inhibited, neurons survive, and therefore, promotion of the regeneration of neurons of the damaged region is expected in the long run. Accordingly, FAM19A5 may be used to objectively and quantitatively diagnose a progress state of disease caused by central nervous system damage.

Therefore, FAM19A5 may be used as a biomarker for diagnosing degenerative brain disease due to central nervous system damage or central nervous system disease.

The term "central nervous system damage" in this specification includes all types of central nervous system damage causing destruction or degeneration of cerebrospinal cells. Traumatic brain injury, amyotrophic lateral sclerosis, and the like may be exemplified, but the damage is not limited thereto.

The term "degenerative brain disease or central nervous system disease" refers to degenerative brain disease or central nervous system disease caused by gliosis resulting from damage of the central nervous system. Examples of such disease include Alzheimer's disease, Huntington's disease, Parkinson's disease, stroke, or brain tumor, but the disease is not limited to any specific type of disease.

The term "diagnosis" refers to determination of a pathologic state. In view of the object of the present invention, the diagnosis refers to the fact that expression of FAM19A5, a diagnosis marker of central nervous system damage, degenerative brain disease, or central nervous system disease is determined to identify occurrence, progress, and alleviation of central nervous system damage, degenerative brain disease, and central nervous system disease.

The term "diagnosis marker" refers to a material capable of separately diagnosing cells of central nervous system damage, degenerative brain disease, or central nervous system disease from normal cells, and includes organic biomolecules such as polypeptides, or nucleic acids (for example, mRNA), lipids, glycolipids, glycoproteins, and sugars (monosaccharides, disaccharides, oligosaccharides, and the like) which increase or decrease in cells of central nervous system damage, degenerative brain disease, or central nervous system disease, compared to normal cells. The diagnosis marker provided in the present invention for central nervous system damage, degenerative brain disease, or central nervous system disease may be a protein that is expressed from FAM19A5 genes of which the expression increases in cells of central nervous system damage, degenerative brain disease, or central nervous system disease, compared to normal cells.

The composition for diagnosing central nervous system damage, degenerative brain disease, or central nervous system disease of the present invention includes an agent for measuring the expression level of mRNA of FAM19A5 genes or the amount of protein expressed. As such an agent, oligonucleotides having a sequence complementary to FAM19A5 mRNA, for example, a primer or a nucleic acid probe that specifically binds to FAM19A5 mRNA, and antibodies specific to FAM19A5 proteins may be included.

The primer refers to a single-stranded oligonucleotide that may serve as a starting point of template-directed DNA synthesis under appropriate conditions (that is, four types of different nucleoside triphosphates and polymerization enzymes) in an appropriate temperature and an appropriate buffer solution. The appropriate length of the primer may be changed by various factors, for example, temperature, and usage of the primer. Also, the sequence of the primer need not have a completely complementary sequence to the sequence of the template. It is sufficient that the sequence have sufficient complementarity in a range in which sequences may be hybridized and the function of the primer may be performed. Therefore, the primer of the present invention need not have a completely complementary sequence to the nucleotide sequence of the genes serving as the template. It is sufficient that the sequence have sufficient complementarity in a range in which sequences hybridize and the function of the primer may be performed. Also, the primer of the present invention may be preferably used in gene amplification reactions. The amplification reaction refers to a reaction of amplifying nucleic acid molecules. Such amplification reactions of genes are well-known in the related art, and may include, for example, polymerase chain reaction (PCR), reverse transcription polymerase chain reaction (RT-PCR), ligase chain reaction (LCR), transcription-mediated amplification (TMA), and nucleic acid sequence based amplification (NASBA).

The nucleic acid probe, which refers to a natural or modified monomer or a linear linked oligomer including a deoxyribonucleotide and a ribonucleotide, is able to specifically hybridize with a target nucleotide sequence, and is naturally occurring or artificially synthesized. The probe, according to the present invention, may be a single chain, and preferably, be an oligodeoxyribonucleotide. The probe of the present invention may include natural dNMP (that is, dAMP, dGMP, dCMP, and dTMP), and nucleotide analogues or derivatives. Also, the probe of the present invention may include a ribonucleotide. For example, it may include backbone-modified nucleotides, such as, peptide nucleic acid (PNA) (M. Egholm et al., Nature, 365:566-568 (1993)), phosphorothioate DNA, phosphorodithioate DNA, phosphoramidate DNA, amide-linked DNA, MMI-linked DNA, 2'-O-methyl RNA, alpha-DNA and methylphosphonate DNA, a sugar-modified nucleotide for example, 2'-O-methyl RNA, 2'-fluoro RNA, 2'-amino RNA, 2'-O-alkyl DNA, 2'-O-allyl DNA, 2'-O-alkynyl DNA, hexose DNA, pyranosyl RNA and anhydrohexitol DNA, nucleotides having a nucleotide variation, for example, C-5 substituted pyrimidine (a substituent includes fluoro-, bromo-, chloro-, iodo-, methyl-, ethyl-, vinyl-, formyl-, ethnyl-, propynyl-, alkynyl-, thiazolyl-, imidazolyl-, and pyridyl-), 7-deazapurine having a C-7 substituent (a substituent includes fluoro-, bromo-, chloro-, iodo-, methyl-, ethyl-, vinyl-, formyl-, alkynyl-, alkenyl-, thiazolyl-, imidazolyl-, and pyridyl-), inosine, and diaminopurine.

As antibodies specific to FAM19A5, polyclonal antibodies, monoclonal antibodies, human antibodies, and humanized antibodies may be used.

Examples of fragments of the antibody include Fab, Fab', F(ab')2, and Fv fragments; a diabody; linear antibodies (Zapata et al., Protein Eng. 8(10):1057-1062 (1995)); single chain antibody molecules; multispecific antibodies formed from antibody fragments, and the like.

When antibodies are decomposed by papain, two identical antigen-binding fragments, "Fab" fragment having a single antigen binding site and the remaining "Fc" fragment, are generated. When pepsin treatment occurs, an F(ab')2 fragment having two antigen binding sites and still capable of cross-linking to the antigen is generated. Fv is a small antibody fragment produced that includes a complete antigen recognizing and binding region. This region is composed of a dimer of one heavy chain and one light chain variable region, and is tightly coupled by non-covalent bonds.

A method of preparing polyclonal antibodies is known for those skilled in the art. Polyclonal antibodies may be prepared by injecting an immunizing agent into mammals one or more times, and as necessary, an immunoadjuvant may be simultaneously injected. Typically, the immunizing agent and/or the immunoadjuvant are subcutaneously or intraperitoneally injected into mammals several times. The immunizing agent may be a protein of the present invention or a fusion protein thereof. When a protein known to have immunogenicity and the immunizing agent are injected together into mammals to be immunized, it may be effective.

The monoclonal antibodies featured in the present invention may be prepared by a hybridoma method described in the document (Kohler et al., Nature, 256:495 (1975)), or prepared by a recombinant DNA method (for example, refer to U.S. Pat. No. 4,816,576). For example, the monoclonal antibodies may also be isolated from a phage antibody library using a technique described in the document (Clackson et al., Nature, 352:624-628 (1991) and Marks et al., J. Mol. Biol., 222:581-597 (1991)).

The monoclonal antibodies of the present invention specifically include "chimera" antibodies in which a part of a heavy chain and/or a light chain has an identical or homologous sequence corresponding to antibodies derived from specific species or antibodies belonging to a specific antibody class or subclass, but the rest of the chain(s) has antibodies derived from different species, or antibodies belonging to a different antibody class or subclass, or is identical or homologous to fragments of such antibodies, as long as a desired activity is exhibited (Morrison et al., Proc. Natl. Acad. Sci. USA, 81:6851-6855 (1984)).

"Humanized" types of non-human (for example, the Murinae) antibodies include a chimera immunoglobulin having a minimum sequence derived from a non-human immunoglobulin, an immunoglobulin chain, or fragments thereof (for example, Fv, Fab, Fab', F(ab')2 or other antigen binding sequences of antibodies). In most cases, the humanized antibodies include a human immunoglobulin (receptor antibodies) in which a residue of a complementarity determining region (CDR) of a receptor is substituted with a CDR residue of non-human species (donor antibodies), such as rats, mice, or rabbits, which have a desired specificity, affinity, and capability. In some cases, an Fv framework residue of the human immunoglobulin is substituted with a corresponding non-human residue. Also, the humanized antibodies may include receptor antibodies or a residue not found in the introduced CDR or framework sequence. In general, the humanized antibodies substantially include at least one, and generally, two or more variable domains. Here, all or substantially all CDR regions correspond to regions of the non-human immunoglobulin, and all or substantially all FR regions correspond to regions of human immunoglobulin sequences. In addition, the humanized antibodies include at least a part of an immunoglobulin constant region (Fc), and generally, a part of a human immunoglobulin region (Presta, Curr. Op. Struct. Biol. 2:593-596 (1992)).

The composition for diagnosing central nervous system damage, degenerative brain disease, or central nervous system disease of the present invention may be included in the form of a kit.

The kit may include the primer, the probe, or the antibodies that may be used to measure the expression level of FAM19A5 genes or an amount of proteins. Definitions thereof are the same as those in the above description.

When the kit is applied to a PCR amplification process, reagents necessary for PCR amplification, for example, a buffer solution, DNA polymerase (for example, thermostable DNA polymerase obtained from *Thermus aquaticus* (Taq), *Thermus thermophiles* (Tth), *Thermus filiformis*, *Thermis flavus*, *Thermococcus literalis* or *Pyrococcus furio-* sus (Pfu)), a DNA polymerase cofactor, and dNTPs may be optionally included. When the kit is applied to an immunoassay, it may optionally include secondary antibodies and a labeled substrate. Further, the kit according to the present invention may be manufactured in multiple separate packages or compartments including the above reagent components.

Also, the composition for diagnosing central nervous system damage, degenerative brain disease, or central nervous system disease of the present invention may be included in the form of a microarray.

In the microarray of the present invention, the primer, the probe, or the antibodies that may be used to measure the expression level of the FAM19A5 protein or gene encoding the protein are used as hybridizable array elements, and fixed on a substrate. A preferred substrate may include, for example, a film, a filter, a chip, a slide, a wafer, a fiber, a magnetic bead or nonmagnetic bead, gel, tubing, a plate, a polymer, a microparticle, or a capillary, as an appropriately robust or non-robust support. The hybridizable array elements are arranged and fixed on the substrate. Such fixation may be performed by a chemical bonding method or a covalent method involving UV. For example, the hybridizable array element may be coupled to a glass surface that is modified to include an epoxy compound or an aldehyde group, or be coupled to a polylysine coating surface by UV. In addition, the hybridizable array element may be coupled to the substrate through a linker (for example: an ethylene glycol oligomer and diamine).

Meanwhile, when a sample applied to the microarray of the present invention is a nucleic acid, the sample may be labeled and hybridized with an array element on the microarray. Hybridization conditions may be variable, and detection and analysis of a degree of hybridization may be variously performed according to a labeling material.

Also, the present invention provides a method of diagnosing central nervous system damage, degenerative brain disease, or central nervous system disease using a method of measuring the expression level of the FAM19A5 gene or protein, and more specifically, the method includes (a) measuring the expression level of FAM19A5 genes or the amount of expressed protein from a biological sample of a patient suspected of having central nervous system damage, degenerative brain disease, or central nervous system disease; and (b) measuring the expression level of genes or the amount of expressed protein from a normal control group sample and comparing the result with the measurement result of (a).

A method of measuring an expression level of genes or an amount of protein in the above description may use a known technique, including a known process of separating mRNA or proteins from a biological sample.

The biological sample refers to a sample collected from a body that has a different gene or protein expression level compared to the occurrence or a degree of progress of central nervous system damage, degenerative brain disease, or central nervous system disease from a normal control group. Examples of the sample may include tissue, cells, blood, serum, plasma, saliva, and urine, but the sample is not limited thereto.

When the expression level of the genes is measured, the level of mRNA is preferably measured. As a method of measuring the level of mRNA, RT-PCR, real time RT-PCR, an RNase protection assay, a Northern blot, a DNA chip, and the like may be used, but the method is not limited thereto.

When the protein level is measured, antibodies may be used. In this case, the FAM19A5 protein in a biological sample and antibodies specific thereto form a conjugate, that is, an antigen-antibody complex. The amount of antigen-antibody complex generated may be quantitatively measured by the size of the signal produced by a detection label. Such a detection label may be selected from a group consisting of an enzyme, a fluorescent material, a ligand, a light-emitting material, a microparticle, a redox molecule, or a radioactive isotope, but the label is not limited thereto. An analysis method of measuring a protein level includes a Western blot, ELISA, radioimmunoassay analysis, radioimmunodiffusion, an Ouchterlony immunodiffusion method, rocket immunoelectrophoresis, tissue immunostaining, an immunoprecipitation assay, a complement fixation assay, FACS, a protein chip, and the like, but the method is not limited thereto.

Therefore, using the detection methods, the present invention may determine the amount of mRNA or protein expressed in a control group, and the amount of mRNA or protein expressed in a patient suspected of having central nervous system damage, degenerative brain disease, or central nervous system disease. The results can then be compared with each other to diagnose occurrence, the degree of progress, and the like of central nervous system damage, degenerative brain disease, or central nervous system disease.

Also, in the method of diagnosing central nervous system damage, degenerative brain disease, or central nervous system disease according to the present invention, when the expression level of the FAM19A5 genes or the amount of the expressed proteins, according to the present invention increases compared to the normal control group sample, it may be determined that central nervous system damage, degenerative brain disease, or central nervous system disease is present.

The present invention also relates to a composition for treating early traumatic brain injury containing FAM19A5 (family with sequence similarity 19, member A5).

The present invention also provides a use of FAM19A5 for preparing a pharmaceutical composition for treating early traumatic brain injury.

Initial reactive astrocytes generated after damage due to traumatic brain injury secrete a nerve growth factor that prevents programmed cell death, such as GDNF, and resumes the uptake of glutamic acid to protect neurons. Also, the astrocytes beneficially function by recovering function of the blood-brain barrier, isolating a region in which damage has occurred, and preventing infection of healthy tissues.

Since FAM19A5 generated from neural stem cells is involved in generation of astrocytes rather than neurons, FAM19A5 may promote generation of astrocytes in a brain injury region to treat early brain injury and inhibit the progression of brain injury disease.

Therefore, FAM19A5 may be used as an agent for treating early traumatic brain injury.

A composition for treating early traumatic brain injury of the present invention may include at least one natural or recombinant FAM19A5 protein, FAM19A5 proteins having substantially equivalent physiological activity thereto, transgenic neural stem cells overexpressing FAM19A5 proteins, or astrocytes differentiated from the neural stem cells. Definitions thereof are the same as those in the above description. The natural or recombinant FAM19A5 proteins or FAM19A5 proteins having substantially equivalent physiological activity thereto promote generation of astrocytes in a brain injury region to treat early traumatic brain injury.

Also, the transgenic neural stem cells overexpressing the FAM19A5 protein are directly injected into brain tissue and FAM19A5 proteins are secreted in a brain injury region to promote generation of astrocytes, or promote differentiation from the transgenic neural stem cells into astrocytes to treat early traumatic brain injury. In this case, in order to promote differentiation of the transgenic neural stem cells, a differentiation-inducing factor may be co-administered. Types of differentiation-inducing factor are the same as those in the above description.

When astrocytes differentiated from neural stem cells are directly injected into brain tissue and a large amount of astrocytes are present in a brain injury region, early traumatic brain injury may be treated.

Also, the present invention provides a method of treating early traumatic brain injury of an animal including administering a composition for treating early traumatic brain injury containing a pharmaceutically effective dose of FAM19A5 to a subject.

A pharmaceutical composition and an administration method used in the method of treating early brain injury will be described below, redundant descriptions will not be provided in order to avoid excessive complexity of the present specification.

A subject, into which the composition for treating early traumatic brain injury may be administered, includes all animals, such as dogs, cats, and rats.

The present invention also relates to a composition for preventing or treating degenerative brain disease or central nervous system disease containing an FAM19A5 (family with sequence similarity 19, member A5) inhibitor.

The present invention also provides a use of the FAM19A5 inhibitor for preparing a pharmaceutical composition for preventing or treating degenerative brain disease or central nervous system disease.

Since FAM19A5 promotes generation of astrocytes, which are a type of glial cell, when expression of FAM19A5 mRNA or protein is inhibited in degenerative brain disease or central nervous system disease, in which a large amount of glial cells is expressed, the number of reactive astrocytes decreases due to FAM19A5 inhibition, and proliferation of progenitor cells expressing NG2 (neuron-glial antigen 2) is promoted, axons of neurons near a brain injury region are myelinated, and thereby an FAM19A5 inhibitor may be used to treat degenerative brain disease or central nervous system disease.

Therefore, the composition for preventing or treating degenerative brain disease or central nervous system disease of the present invention may include an agent for decreasing mRNA expression of FAM19A5 genes or expression of protein thereof, or a function or an activity.

The FAM19A5 protein inhibitor may be a peptide or a compound that is coupled to FAM19A5 proteins and regulates a signal of a neural differentiation path. Such an inhibitor may be selected by the following exemplified screening method such as a protein structure analysis, and may be designed using a known method in the related art.

Also, the protein inhibitor may use polyclonal antibodies, monoclonal antibodies, human antibodies, and humanized antibodies for FAM19A5 proteins, and definitions of the antibodies are the same as those in the above description.

When signal transduction of a neural differentiation pathway of receptors in cells is regulated using the antibodies, degenerative brain disease or central nervous system disease may be prevented or treated.

A function or activity inhibitor of FAM19A5 protein of the present invention may be delivered by liposomes, viruses, a gene gun, a polymer, ultrasound, or electric shock, but the delivery method is not limited thereto.

The FAM19A5 genes may be DNA encoding the gene or mRNA transcripted therefrom. Therefore, the inhibitor of the genes may be an inhibitor that is coupled to the gene itself to prevent transcription or coupled to mRNA transcripted from the gene to prevent translation of the mRNA.

Therefore, the inhibitor of the FAM19A5 gene includes all inhibitors that suppress expression of FAM19A5 genes. For example, such an inhibitor may be a peptide, nucleic acid, a compound, and the like coupled to the gene. The inhibitor may be selected by the following exemplified screening method such as cell-based screening, and may be designed using a known method in the related art.

In a detailed example, the inhibitor may be an antisense-oligonucleotide, siRNA, shRNA, miRNA, or a vector including the same of FAM19A5 genes. Such an antisense-oligonucleotide, siRNA, shRNA, miRNA and a vector including the same may be prepared using a known method in the related art.

The term "siRNA" in the present specification refers to double-stranded RNA molecules inducing RNA interference through cutting the mRNA of a target gene, and requires an RNA strand of a sense sequence having the same sequence as mRNA of the target gene and an RNA strand of an antisense sequence having a sequence complementary thereto.

The siRNA may include the siRNA itself synthesized in vitro or a form that is expressed by inserting a sequence encoding siRNA into an expression vector.

In the present invention, the term "vector" refers to a gene construct including external DNA inserted into a genome encoding a polypeptide.

The vector related to the present invention is a vector in which a nucleic acid sequence inhibiting the gene is inserted into a genome. Examples of a vector may include a DNA vector, a plasmid vector, a cosmid vector, a bacteriophage vector, a yeast vector, or a virus vector.

Also, the antisense strand has a sequence complementary to the FAM19A5 gene or all or some mRNA sequences transcripted from fragments thereof and couples to the mRNA to inhibit expression of the FAM19A5 gene or fragments thereof.

Also, short hairpin RNAi (shRNAi) may be prepared by targeting a common shRNAi sequence area of humans or rats using a general method.

Also, the composition for preventing or treating degenerative brain disease or central nervous system disease of the present invention may further include embryonic neural stem cells or adult neural stem cells in addition to the FAM19A5 inhibitor. Since the FAM19A5 inhibitor regulates proliferation and differentiation of neural stem cells, used together they promote generation of neurons helping tissue recovery, so treatment of degenerative brain disease or central nervous system disease may be further improved.

The present invention also provides a method of treating degenerative brain disease or central nervous system disease of an animal, including administering a composition for preventing or treating degenerative brain disease or central nervous system disease containing a pharmaceutically effective dose of the FAM19A5 inhibitor to a subject.

Since the pharmaceutical composition and the administration method used in the treatment of degenerative brain disease or central nervous system disease have been already described above, redundant description will not be provided in order to avoid excessive complexity of the present specification.

Meanwhile, a subject to which the pharmaceutical composition for preventing or treating degenerative brain disease or central nervous system disease may be administered may include all animals, for example, non-human animals such as dogs, cats, and rats.

Also, a medicine composition of the present invention may further include a pharmaceutically acceptable carrier.

The pharmaceutically acceptable carrier includes a carrier and a vehicle that are commonly used in the field of medicine, and specifically, includes an ion exchange resin, alumina, aluminum stearate, lecithin, a serum protein (for example, human serum albumin), a buffer material (for example, various phosphates, glycine, sorbic acid, potassium sorbate, and a partial glyceride mixture of saturated vegetable fatty acid), water, salts or electrolytes (for example, protamine sulfate, disodium hydrogen phosphate, potassium hydrogen phosphate, sodium chloride, and zinc salts), colloidal silica, magnesium trisilicate, polyvinylpyrrolidone, a cellulosic substrate, a polyethylene glycol, sodium carboxymethyl cellulose, polyarylate, wax, a polyethylene glycol, lanolin, and the like, but the carrier is not limited thereto.

Also, the composition of the present invention may further include a lubricant, a wetting agent, an emulsifying agent, a suspending agent, a preservative, and the like in addition to the above components.

As an aspect, the composition according to the present invention may be prepared as an aqueous solution for parenteral administration. Preferably, Hank's solution, Ringer's solution, or a buffer solution such as a physically buffered salt solution, may be used. An aqueous injection suspension may include a substrate that may increase the viscosity of the suspension such as sodium carboxymethyl cellulose, sorbitol, or dextran.

The composition of the present invention may be systemically or locally administered and may be formulated in an appropriate formulation using a known technique for administration. For example, when the composition is administered orally, the composition may be mixed with an inert diluent or an edible carrier, sealed in a hard or soft gelatin capsule, or compressed into a tablet, and then administered. In oral administration, the active compound may be mixed with an excipient and used in the form of an intake tablet, a buccal tablet, a troche, a capsule, an elixir, a suspension, syrup, a wafer, and the like.

Various formulations for injection, parenteral administration, and the like may be prepared by a known technique in the related art or a commonly used technique. Since FAM19A5 is very soluble in a saline or a buffer solution, FAM19A5 is stored in a freeze-dried state, and then an effective dose of FAM19A5 may be formulated in a saline or a buffer solution for administration in an appropriate form for intravenous injection, subcutaneous injection, intramuscular injection, intraperitoneal injection, percutaneous administration, and the like immediately before administration.

An effective dose of the active ingredient of the medicine composition of the present invention refers to an amount that is necessary to prevent, inhibit, or alleviate disease.

Therefore, the effective dose may be regulated according to various factors such as disease type, severity of disease, the active ingredient contained in the composition and types and contents of other components, types of formulation, a patient's age, weight, general health condition, and gender, diet, administration time, administration route, secretion rate of the composition, treatment period, and medicine used by the patient at the same time. For example, when administration is performed once or several times a day in adults and the inhibitor of the present invention is administered once or several times a day, 0.1 ng/kg to 10 g/kg of a compound, 0.1 ng/kg to 10 g/kg of polypeptides, proteins or antibodies, and 0.01 ng/kg to 10 g/kg of an antisense-oligonucleotide, siRNA, shRNAi, or miRNA may be administered, but the dose is not limited thereto.

The present invention also provides a method of screening for a preventive or therapeutic medicine for brain disease or central nervous system disease, including contacting FAM19A5 (family with sequence similarity 19, member A5) genes with a candidate material in vitro, and determining whether the candidate material promotes or inhibits expression of the genes.

The present invention also provides a method of screening a preventive or therapeutic medicine for brain disease or central nervous system disease, including contacting FAM19A5 (family with sequence similarity 19, member A5) proteins with a candidate material in vitro, and determining whether the candidate material promotes or inhibits a function or an activity of the protein.

According to the screening method of the present invention, first, a candidate material to be analyzed comes in contact with cells of brain disease or central nervous system disease including the gene or protein.

According to a conventional selecting method, the candidate material may include a material promoting or inhibiting transcription into mRNA and translation into proteins in FAM19A5 gene sequences, a material proposed to have a possible medical application promoting or inhibiting a function or an activity of FAM19A5 proteins, or randomly selected individual nucleic acids, proteins, peptides, other extracts, natural products, compounds, and the like.

Then, the amount of gene expression, the amount of protein, or activity of protein may be measured in candidate material-treated cells. In the measurement result, when an increase or a decrease in the amount of gene expression, the amount of protein, or the activity of the protein is measured, the candidate material may be determined as a material capable of treating or preventing brain disease or central nervous system disease.

In the above description, measurement of the amount of gene expression, the amount of protein, or the activity of the protein may be performed by various methods known in the related art, for example, RT-PCR, real time polymerase chain reaction, a Western blot, a Northern blot, an enzyme linked immunosorbent assay (ELISA), radioimmunoassay analysis (RIA), radioimmunodiffusion, an immunoprecipitation assay, and the like, but the method is not limited thereto.

A candidate material exhibiting an activity promoting gene expression or promoting a function of proteins, and conversely, a candidate material exhibiting an activity inhibiting gene expression or inhibiting a function of proteins are obtained by the screening method of the present invention. The former material may be a candidate material of a therapeutic agent for early traumatic brain injury. The later material may be a candidate material of a therapeutic agent for degenerative brain disease or central nervous system disease.

Such a therapeutic agent candidate material for degenerative brain disease or central nervous system disease may serve as a leading compound in the later development process of a therapeutic agent for degenerative brain disease or central nervous system disease. When the leading compound transforms and optimizes a structure thereof such that functions of FAM19A5 genes or proteins expressed therefrom may be promoted or inhibited, a novel therapeutic agent for degenerative brain disease or central nervous system disease may be developed.

Contents related to genetic engineering technology in the present invention may be clearly understood from contents disclosed in a book by Sambrook (Sambrook, et al. Molecular Cloning, A Laboratory Manual, Cold Spring Harbor laboratory Press, Cold Spring Harbor, N.Y. (2001)) and Frederick (Frederick M. Ausubel et al., Current protocols in molecular biology volume 1, 2, 3, John Wiley & Sons, Inc. (1994)).

Advantages and features of the present invention and a method of achieving them will be clearly understood with reference to examples which will be described in detail. However, the present invention is not limited to the following disclosed examples but may be implemented in different forms. The examples are only provided to completely disclose the present invention and completely inform those skilled in the art of the scope of the present invention, and the present invention is defined by the appended claims.

Example 1

Finding New Secretory FAM19A5 Peptide Using Bioinformatics

The task of screening FAM19A5 genes was performed through a bioinformatics approach model. The inventors downloaded open reading frames (ORFs) of about 50,000 species of human genome genes from Ensembl (http://www.ensembl.org/index.html) and UniprotKB (http://www.uniprot.org/uniprot). In order to identify whether genes having possible physiological active peptides were among them, genes (secretome) of about 2,000 species that may be secreted from cells were screened using a Signal P3.0 program. Based on UniprotKB information, screened ORFs were analyzed. The result showed that ORFs of about 600 species were determined as genes (peptidome) encoding peptides. Among them, 560 species were genes of which functions had been already known, but the remaining 40 species were genes of which functions had not yet been discovered and encode new peptides.

FAM19A5 genes among them were found in various vertebrates including humans. FAM19A5 includes a gene sequence encoding a typical signal peptide of an amino terminus as a signal that may be extracellularly secreted, and subsequently, includes an amino acid sequence of mature FAM19A5. In particular, amino acid sequences of FAM19A5 proteins were very well conserved among the species (FIG. 1A). A comparative genomic analysis method described above is recognized as a reliable experimental model capable of verifying whether a newly found novel gene has a substantial function [Robbins, *J Comput Biol* 3:465-478, 1996]. Meanwhile, according to results of conventional art documents, while there is a paper in which CC-chemokine genes were identified to be greatly expressed in brain tissue afflicted with Alzheimer's disease and an identified mechanism in which MIP-la as a CC-chemokine family gene, proliferates glial cells and aggravates degenerative brain disease was analyzed, a phylogenetic tree (FIG. 1B) may show that FAM19A family genes form a distinctly different branch from the CC-chemokine family genes [MengQi Dia et al., American Journal of Pathology, 1998].

Example 2

Verification of Expression of FAM19A5 Genes in Various Tissues by Reverse Transcription Polymerase Chain Reaction (RT-PCR)

Six-week old black male mice (C57BL/6, mouse) were bought from Daehan Bio Link Co., Ltd. (http://www.dhbiolink.com). The bought mice were raised in a mouse cages in which adequate feed and water were given, a temperature of 20 to 24° C. was maintained, and a humidity of 40 to 70% was maintained. In addition, these wild-type mice were kept on a 12/12 Light/Dark cycle (light on at 8:00 am and light off at 8:00 pm). All experiments were designed to use the fewest number of mice, an anesthesia method was performed according to animal experiment ethics to minimize pain of the mice used in the experiment, and this was approved by Animal Care and Use Committee of the Korea University (KUIACUC-08).

All RNAs of each corresponding tissue from mice were extracted, and then complementary DNA (cDNA) was prepared using reverse transcriptase and a random hexamer. Then, a polymerase chain reaction (PCR) was performed using a corresponding primer, and an mRNA distribution of mouse tissues was observed. Information on primers used in PCR is listed in Table 1.

Figure 2:
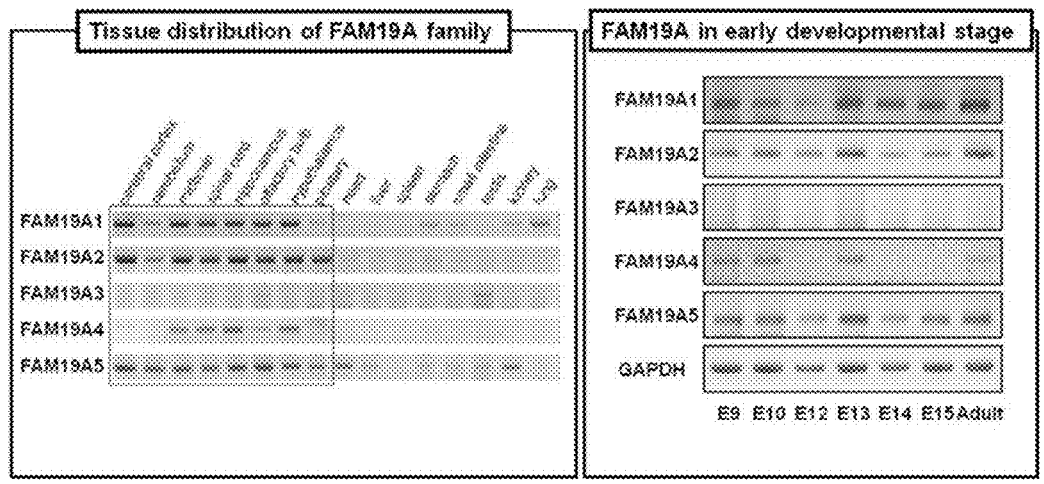
FIG. 2 shows mRNA expression patterns (A) of FAM19A family genes in various mouse tissues and mRNA expression patterns (B) of FAM19A family genes for each developmental stage through reverse transcription polymerase chain reaction (RT-PCR).

As shown in FIG. 2, all types of FAM19A family genes except the FAM19A3 gene were brain-specifically expressed. Also, expression of FAM19A family genes was observed even in the early developmental stage.

TABLE 1

| Target gene | Primer sequences | PCR product Size (bps) | Positions | Accession number |
|---|---|---|---|---|
| FAM19A1 | up: ATG GCA ATG GTC TCT GCA | 402 | 437-838 | NM 182808 |
| | down: TTA GGT TCT TGG GTG AAT | | | |
| FAM19A2 | up: ATG ATC ACC AAG ATG AAT | 408 | 1668-2075 | NM 182807 |
| | down: TTA ATG GGT TAC CCT AGT TG | | | |
| FAM19A3 | up: ATG GAG AGG CCC ACC AGC | 399 | 590-988 | NM 183224 |
| | down: TTA CCG TGT GAC CTT GGT | | | |

TABLE 1-continued

| Target gene | Primer sequences | PCR product Size (bps) | Positions | Accession number |
|---|---|---|---|---|
| | G | | | |
| FAM19A4 | up: ATG AGA GTC TGT GCT AAG T<br>down: CTA CCG GGT CAC CTT GGT | 408 | 423-830 | NM 177233 |
| FAM19A5 | up: ATG CAG CTC CTG AAG GCG CT<br>down: TCA GGA GAC CGT GGT GGT CT | 378 | 167-544 | NM 134096 |

Example 3

Verification of Expression of FAM19A5 Genes for Each Developmental Stage by In Situ Hybridization In order to determine expression patterns of FAM19A family genes in the cerebral cortex during the development process, in situ hybridization was used to compare amounts of mRNA. Wistar rats were managed in the same manner as the above method. The rats, on embryonic day 14 (E14) before birth, to 21 days after birth (postnatal day, P21) were sacrificed (decapitation) to obtain the brain from the skull. Since rats, before birth, have a larger body size than mice, which is a different type of experimental rat, rats were easier to handle in the experiment and used to compare FAM19A5 gene expression for each developmental stage.

The extracted brain was moved and frozen in a cold isopentane solution on dry ice. Frozen brain tissues were sliced (sectioned) at 12 μm, attached (Thaw-mounted) to a slide glass coated with TESPA (Sigma-Aldrich Co., Llc., St. Louis, Mo., USA), and fixed in a phosphate buffered saline (PBS) solution containing 4% paraformaldehyde. Then, an acetylating reaction was performed using 0.1M triethanolamine/0.9% NaCl (pH 8.0) solution containing 0.25% acetic anhydride. Then, ethanol and a chloroform solution were used to perform dehydration and degreasing process, and drying was performed in air. Meanwhile, the sectioned tissues were hybridized at 55° C. using a probe labeled with $^{35}S$, and washed with a 2×SSC solution at normal temperature. The slide was treated with RNA-degrading enzyme (RNase), and then the slide was sequentially washed with 2×SSC, 1×SSC, 0.5×SSC, 0.1×SSC solutions containing 1 mM dithiothreitol at normal temperature for 10 minutes each. Finally, the tissue sections were dehydrated, dried in air, and then the slide glass containing brain tissue sections was exposed to an X-ray film (Biomax MR, Eastman Kodak Co., Rochester, N.Y., USA).

Meanwhile, all RNAs were extracted from the cerebral cortex of adult rats in order to generate a probe, cDNA was prepared using reverse transcriptase and a random hexamer primer, and then T-vector (Promega Corp., Madison, Wis., USA) cloning was performed. Information on primers used in PCR was listed in Table 2. The cloned T-vector was used as a template, an in vitro transcription system (Promega Corp., Madison, Wis., USA) was performed with [$^{35}S$]UTP (Amersham Pharmacia Biotech Inc., Piscataway, N.J., USA), and antisense riboprobes of a generated radio label were purified and used the present hybridized reaction.

TABLE 2

| Target gene | Primer sequences | PCR product Size (bps) | Positions | Accession number |
|---|---|---|---|---|
| FAM19A5 | up: ATG CAG CTC CTG AAG GCG<br>down: TCA GGA GAC CGT GGT GGT | 399 | 13-411 | NM 001191991 |

A dissection plan of the rat's brain was screened by an overall coronal plane and sagital plane from rostral in which the olfactory bulb is located to caudal in which the cerebellum is located.

Figure 3:
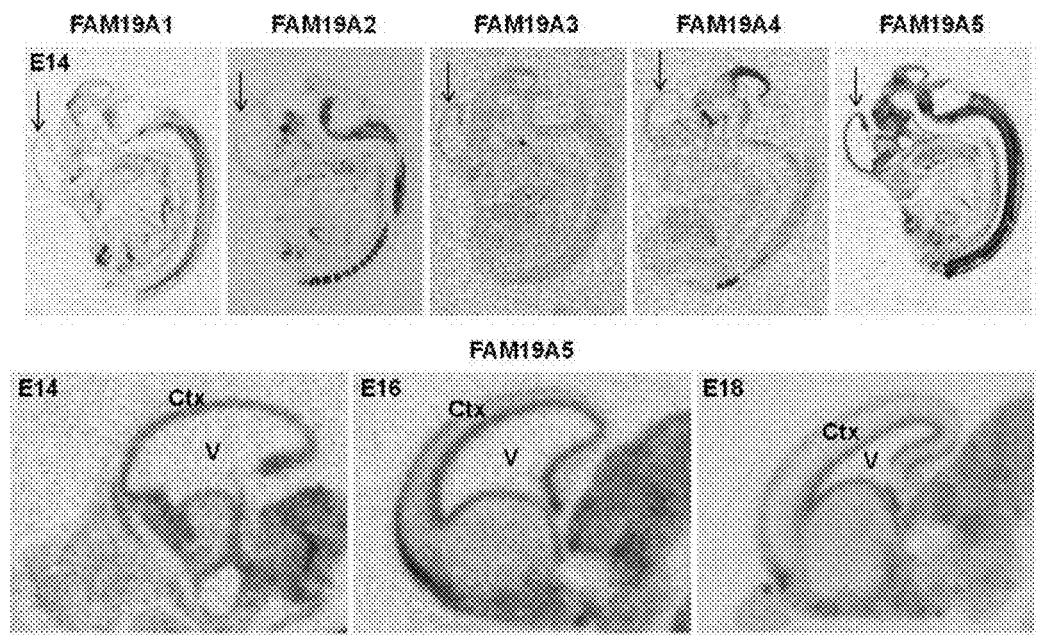
FIG. 3 shows the results obtained by measuring expression of FAM19A5 mRNA in the ventricular zone and spinal cord of rats for each developmental stage using in situ hybridization.

As shown in FIG. 3, in mRNA expression of FAM19A family genes, only FAM19A5 mRNA was strongly distributed in the ventricular zone and the spinal cord. On embryonic days 14 (E14) and 16 (E16) before birth, FAM19A5 was strongly expressed only in the ventricular zone. FAM19A5 was still highly expressed on embryonic day 18 (E18) in the ventricular zone and the subventricular zone and much more weakly expressed in the cortical plate in which differentiated neurons were included.

FAM19A5 genes were strongly expressed in two regions of the central nervous system known to have a distributed population of neural stem cells. This means that FAM19A5 proteins are important in formation of a complete central nervous system and demonstrates for the first time that FAM19A5 proteins may be involved in generation of neurons and glial cells constituting the central nervous system.

Example 4

Preparation of FAM19A5-Specific Antibody

In order to prepare antibodies capable of specifically recognizing FAM19A5 proteins, short synthetic FAM19A5 was inoculated into a rabbit to obtain polyclonal antibodies. The antibodies specifically recognized only FAM19A5 among FAM19A family genes that are overexpressed in HEK293T cells (FIG. 4A). Also, when treated with N-glicosidase F, 20 kDa band, a mature protein of FAM19A5, disappeared, which was determined as an N-glycosylated form (FIG. 4B). Also, each antibody specifically recognized HEK293T cells expressing FAM19A5 (His-tagged), which was observed using immunocytochemistry (FIG. 4C).

Example 5

Measurement of FAM19A5 Protein Expression During Development Process by Immunohistochemistry In order to determine whether patterns of FAM19A5 protein expression after translation similarly appear, immunohistochemistry was used. Mice were managed in the same manner as the above method. Mice on embryonic days 12 (E12) to 18 (E18) before birth were sacrificed to obtain the brain from the skull. The extracted brain was fixed (post-fixation) in phosphate buffered saline containing 4% paraformaldehyde for 24 hours to 48 hours and treated with phosphate buffered saline containing 30% sucrose for 24 hours. Then, the brain was placed in a mold for brain tissues and frozen on dry ice with an OCT composite containing 30% of a sugar solution, and kept at −80° C. before the brain was used.

In order to determine the regions and intensity of FAM19A5 protein expression in the mouse's brain by immunohistochemistry, anti-FAM19A5 that is a polyclonal antibody prepared in Example 4 was used as an antibody that may react with the FAM19A5 protein. The mouse's frozen brain tissue was sliced at 40 µm using a cryostat microtome. The brain tissue sections were washed with a PBS solution for 30 minutes and blocked for one hour using a PBS-T solution (a solution in which 10% TritonX-100 is contained in phosphate buffered saline) containing 10% serum chloride. In the final fluorescence image to be shown, in order to avoid near non-specific antigen-antibody reactions and more accurately distinguish an FAM19A5-specific expression region, a ratio of an FAM19A5 antibody:blocking solution was set to 1:500. FAM19A5 antibodies and antigens were reacted at 4° C. overnight or at normal temperature (25° C.) for about 3 hours. After a primary antibody-antigen reaction was completed, the brain tissue sections were washed three times with phosphate buffered saline for 10 minutes each time. Then, as a secondary antibody, FITC-coupled anti-rabbit IgG (Invitrogen, USA) was diluted at a ratio of 1:500 and used. After a secondary antibody-antigen reaction was completed, the brain tissue sections were washed three times with a phosphate buffered saline solution for 10 minutes each time and then the tissue was evenly mounted on the slide glass (mounting). The tissues were dried at room temperature for about 5 minutes, a crystal/mount solution (Biomeda Corp., USA) was applied onto the tissues, and a cover glass was used to cover to prepare a specimen. A fluorescence image of the prepared specimen was obtained using a confocal microscopy (Zeiss LSM 510 confocal microscopy).

Since neural stem cells or neural progenitor cells have an intermediate filament protein named nestin, nestin was used as a marker [Lendahl et al., Cell 60:585-595, 1990]. In the early developmental stage, it was observed that nestin had already been expressed in the neural plate before a neural tube was formed [Woodbury et al., J Neurosci Res 61:364-370, 2000]. Since neuroblasts have a microtubule-associated protein doublecortin (DCX), DCX was used as a marker. Nestin and DCX used CY3-coupled anti-mouse and goat IgG (Invitrogen, USA) diluted at a ratio of 1:500 as a secondary antibody.

Figure 5:
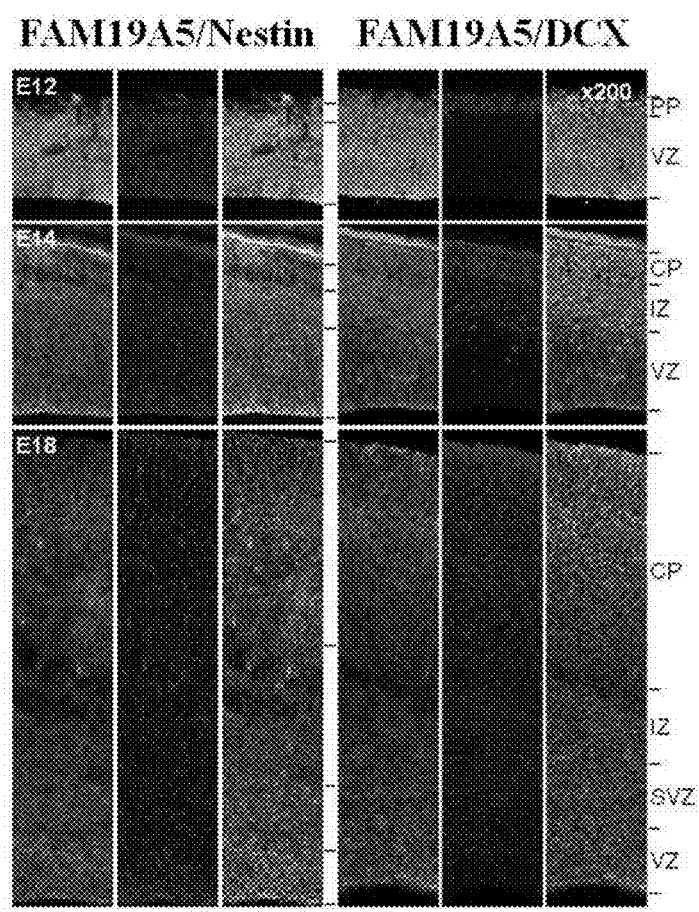
FIG. 5 shows the results obtained by measuring expression of FAM19A5 peptides in the ventricular zone of mouse for each developmental stage using immunohistochemistry.

As shown in FIG. 5, interestingly, as in the experiment result using in situ hybridization, FAM19A5 proteins were strongly expressed in the ventricular zone, even at a protein level. On embryonic day 12 (E12) which is a period in which progenitor cells being divided are mainly distributed in the ventricular zone, FAM19A5 peptides were mainly expressed throughout the ventricular zone and still highly expressed on embryonic days 14 (E14) and 18 (E18). An amount of expression in the cortical plate was much lower than in the result using in situ hybridization. In the progenitor cells containing nestin, FAM19A5 proteins were shown in the punctate form. In the neuroblasts containing DCX, weak expression thereof was shown. In some genes, due to a preparing process after transcription or post-translation, levels of protein expression and mRNA expression may differ [Wellington et al., Lab Invest 82:273-283, 2002], but the same expression pattern was shown in the present experiment.

The results of Example 5 in addition to the results of Example 3 proposed identification, an expression position, an expression level, or an expression intensity of FAM19A5 proteins in brain tissues during a development process. FAM19A5 was considered to be expressed in neural stem cells constituting the central nervous system and to be involved in generation of neurons and glial cells.

Example 6

Measurement of FAM19A5 Protein Expression in Adult Neural Stem Cells by Immunohistochemistry Similar to mice before birth, the region and intensity of FAM19A5 protein expression were determined in brains of adult mice by immunohistochemistry.

Therefore, 4-week old male mice managed in the above method were intraperitoneally injected with urethane 0.5 cc/100 g for anesthesia, the chest was cut, a Ringer's needle was inserted into the left cardiac ventricular to drain blood with 0.9% of saline solution (200 mL), and the cardiac ventricular was perfused with 0.9% of saline solution (200 mL) containing 4% paraformaldehyde and fixed. The brain of the fixed mice was extracted, fixed using phosphate buffered saline containing 4% paraformaldehyde for 24 hours to 48 hours, and treated with phosphate buffered saline containing 30% of sugar for about 24 hours. Then, the brain was placed in a mold for brain tissue, frozen on dry ice with an OCT composite containing 30% of a sugar solution, and kept at −80° C. before the brain was used. Similar to mice before birth, in order to determine the region and intensity of FAM19A5 protein expression through immunohistochemistry in the adult mouse's brain, FAM19A5 antibodies were used. Also, since adult neural stem cells (ependymal cells and astrocytes) have an intermediate filamentprotein named a glial fibrillary acidic protein (GFAP, Invitrogen, USA), GFAP was used as a marker.

Figure 6:
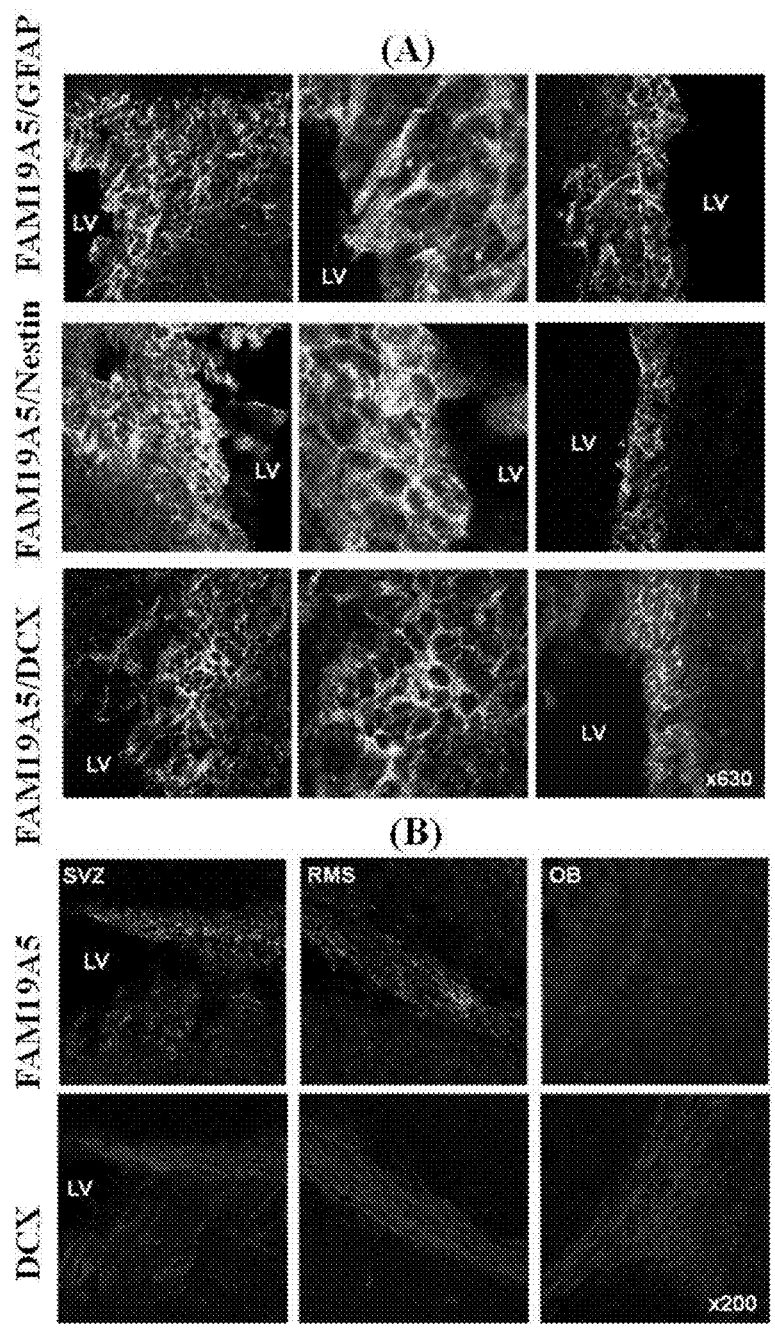
FIG. 6 shows the results obtained by measuring (A) expression of FAM19A5 peptides in neural stem cells and progenitor cells in the subventricular zone of adult mouse, and (B) the degree of expression of FAM19A5 peptides under differentiated conditions using immunohistochemistry.

As shown in FIG. 6A, similar to the experiment result of the developmental stage, a degree of expression of FAM19A5 was high in the subventricular zone (SVZ) that is known to have a distributed population of adult neural stem cells.

Therefore, it may be concluded that expression of FAM19A5 is higher in neural stem cells than neuroblasts.

It was then determined whether an amount of protein of FAM19A5 decreases through differentiated conditions. For this purpose, an experiment was performed focusing on SVZ-RMS-OB tract.

Neuroblasts in the SVZ migrated to the olfactory bulb (OB) through a rostral migratory stream (RMS) and were finally differentiated into mature interneurons. Since FAM19A5 was more highly expressed in the SVZ-RMS than the OB, it was considered that the amount of protein decreases through a differentiation process (FIG. 6B).

Example 7

Measurement of FAM19A5 Expression in Neurospheres Developing from Adult Neural Stem Cells Technology for continuously proliferating neural stem cells improves and therefore a cell mass developing from neural stem cells named neurospheres may be made. Such technology may be used for various experiments and is being used as a useful experiment model that may reversely track properties of neural stem cells [Reynolds and Weiss, Science 255:1707-1710, 1992; Reynolds and Weiss, Dev Biol 275:1-13, 1996].

In order to obtain adult neural stem cells, brains were extracted from 3-week to 8-week old male mice. In order to separate the subventricular zone known to have an adult neural stem cell population, brain matrices were used. Tissues were dissociated into single cells using protease such as dispase (Invitrogen, USA) and papain (Worthington Biochemical Corp., USA). A growth factor such as an epidermal growth factor (EGF, Invitrogen) and a basic fibroblast growth factor (bFGF, Invitrogen) was added to a culture solution, and cells were selectively proliferated to form neurospheres. In addition to adult neural stem cells, a cerebral cortex was separated from a brain of the mouse on embryonic day 12 (E12) before birth, embryonic neural stem cells were selectively cultured using the same method to obtain neurospheres.

Neurospheres composed of adult neural stem cells and neurospheres composed of embryonic neural stem cells were fixed in a culture plate using laminin (Invitrogen, USA) serving as a cell adhesion protein and then immunocytochemistry was performed in order to determine whether FAM19A5 proteins are expressed. The result was fixed in phosphate buffered saline containing 4% paraformaldehyde for 15 minutes and permeabilized with a PBS-T solution (a solution in which 0.5% TritonX-100 is contained in a phosphate buffered saline) for 5 minutes. After blocking for 30 minutes was performed, an antigen-antibody reaction was performed, and a dapi staining method was used to observe nuclei.

FAM19A5 proteins were expressed in most neurospheres. Since the proteins are secretory proteins, the proteins were stained in the punctate form in cytoplasm (FIG. 7).

In addition, in order to know properties of cells expressing FAM19A5 proteins, neurospheres were simultaneously stained with various markers of neural stem cells.

As a result, cells expressing FAM19A5 proteins simultaneously expressed nestin (FIG. 8A). This indicates that neurospheres obtained from neural stem cells are used as a good experiment model for studying FAM19A5.

Also, in order to verify whether FAM19A5 gene expression in neurospheres is stronger than gene expression of other types of the same family, all RNAs were extracted from neurospheres developed from adult neural stem cells. Then, cDNA was prepared using reverse transcriptase and a random hexamer. PCR was performed using a corresponding primer, and an FAM19A5 mRNA distribution in neurospheres was observed. Information on primers used in PCR was listed in Table 1.

As shown in FIG. 8B, FAM19A5 mRNA among FAM19A family genes was more significantly distributed than the other types.

In addition to RT-PCR, a microarray was used to compare degrees of expression of FAM19A family genes. Production of cDNA and labeled-cRNA and a hybridized reaction with an Affymetrix MOE430 v2.0 GeneChip (46 k probe-sets) were performed according to a basic protocol available from Affymetrix, Inc. (www.affymetrix.com). A fluorescent label was used in cDNA synthesis for easy analysis and ChipInspector software (Genomatix Software GmbH) was used for statistical analysis of the amount of expression.

As shown in FIG. 8C, similar to the results in RT-PCR, the amount of expression of FAM19A5 genes was significantly higher than that of other types of genes. In addition, a normalized level is from 4 to 14. In consideration of the fact that a gene distribution of level 10 or more is very rare, the result indicates that FAM19A5 is a gene showing strong expression in neurospheres.

Results of Example 6 and Example 7 strongly suggest that FAM19A5 may serve as an important material in functions of adult neural stem cells and embryonic neural stem cells or in a differentiation process into other types of cells generated therefrom.

Example 8

Numerical Change in Generated Astrocytes According to Analysis of Specific Markers of Neurons and Glial Cells after Neutralization Action of Antibody Against FAM19A5

In order to determine whether FAM19A5 proteins generated and secreted from neural stem cells influence the generation of cells differentiated therefrom, an antibody specific to FAM19A5 was used.

In order to perform a differentiation test, neurospheres were dissociated into single cells using Accutase (Innovative Cell Technologies Inc., USA). 50,000 cells were put into each well of a 24-well plate and maintained in a culture solution containing a growth factor for a day, for stabilization. On the next day, the solution was changed to a differentiation culture solution containing a factor promoting differentiation. Differentiation was induced for 6 days, and FAM19A5 antibodies (500 ng/mL) were simultaneously added as a treatment every day. Western blotting and immunocytochemistry using markers labeling three types of nervous system cells including neurons, astrocytes, and oligodendrocytes were performed.

Figure 9:
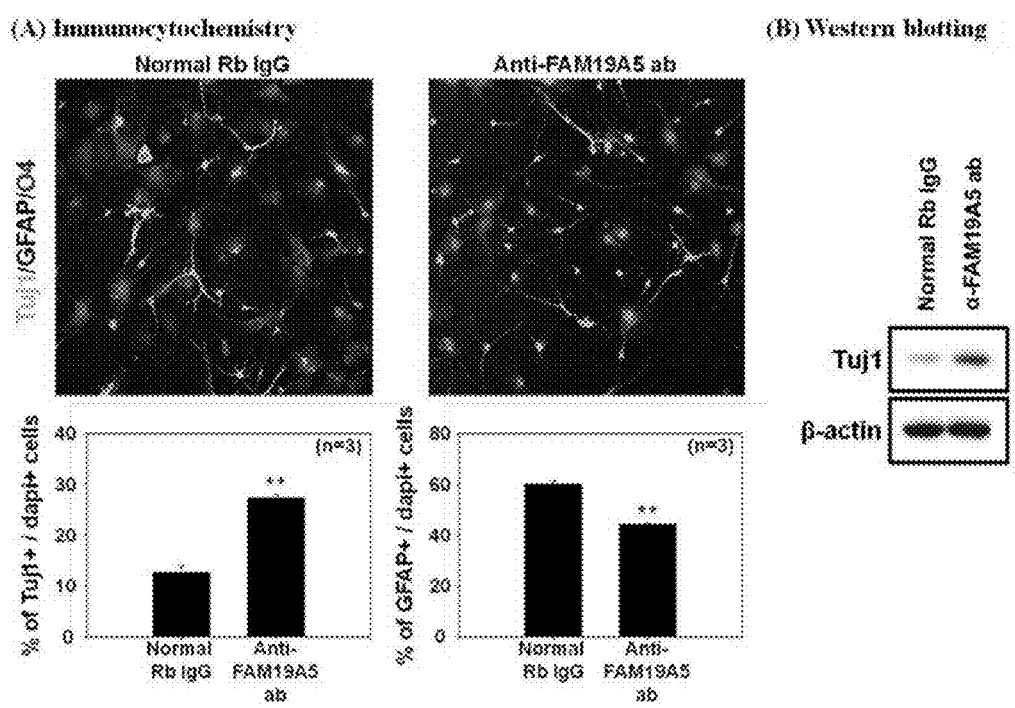
FIG. 9 shows the results obtained by measuring the effect of the differentiation potential of neural stem cells caused by FAM19A5 and a specific antibody thereof using immunocytochemistry (A) and Western blotting (B).

As shown in FIG. 9, interestingly, in an experimental group using a corresponding antibody inducing a neutralization action of FAM19A5 proteins, the number of neurons labeled with Tuj1 increased about two times more than a control group treated with normal Rb IgG, and the number of astrocytes labeled with GFAP decreased correspondingly.

As a result, it may be considered that FAM19A5 proteins may serve as a functional molecule in a differentiation process from stem cells into other types of cells, and particularly, may be involved in promotion of astrocyte generation.

Example 9

Influence of FAM19A5 Peptide and Specific Antibody on Proliferation of Neural Stem Cells In order to determine whether FAM19A5 proteins generated and secreted from neural stem cells influence proliferation, peptides and specific antibodies of FAM19A5 were used. In order to perform a proliferation experiment, neurospheres were dissociated into single cells. 50,000 cells were put into each well of a 24-well plate and a culture solution containing a growth factor was treated with peptides or antibodies. Proliferation was induced for 6 days using the growth factor and FAM19A5 peptides and specific antibodies were simultaneously treated at 500 ng/mL everyday. On the final day, formed neurospheres were dissociated into single cells, and the number of cells was measured.

Figure 10:
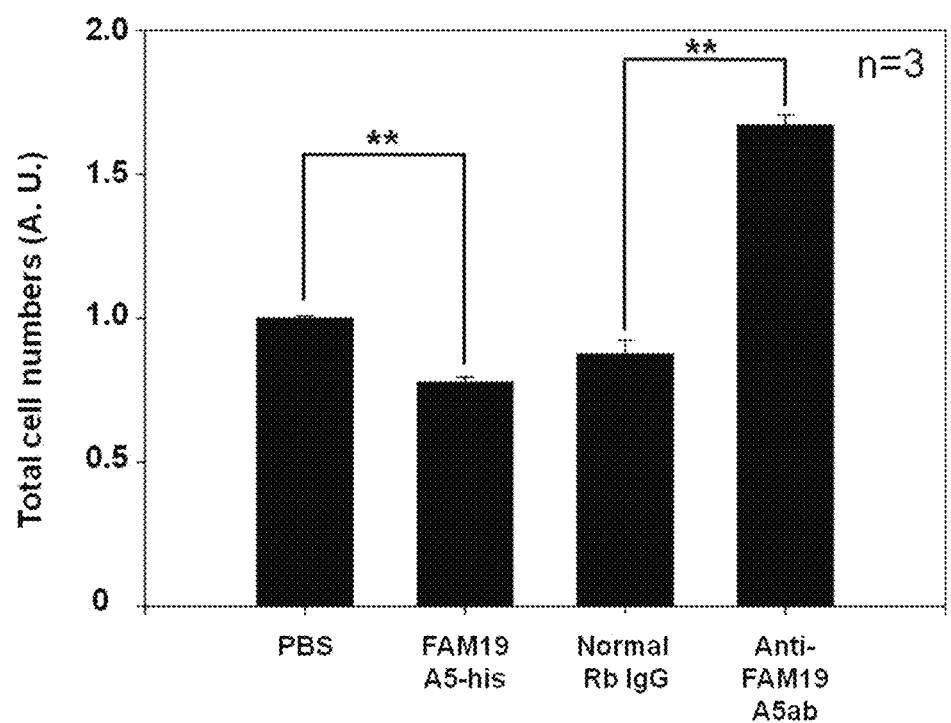
FIG. 10 shows the results obtained by measuring the effect of the proliferation potential of neural stem cells caused by FAM19A5 and a specific antibody.

As shown in FIG. 10, it was observed that proliferation of neural stem cells significantly decreased due to FAM19A5 peptides compared to the control group, and when the specific antibody was added as a treatment, proliferation increased.

Example 10

Quantitative Change in FAM19A5 Proteins in Traumatic Brain Injury (TBI) Mice Model In order to determine whether there is a change in the amounts of FAM19A5 proteins after brain injury, a traumatic brain injury model was used. The head of an 8-week-old mouse was fixed and then an iron bar, sufficiently cooled by liquid nitrogen, was placed on the right side of the skull for one minute. The mouse's skin was sutured through an operation, and the mouse was managed in the same manner as normal mice for 7 days [Moon et al., Neuro report 22:304-308].

Seven days later, intraperitoneal anesthesia was performed on the mouse, the chest was cut, a Ringer's needle was inserted into a left cardiac ventricular to drain blood with 0.9% of normal saline (200 mL), and then the cardiac ventricular was perfused with 0.9% of saline solution (200 mL) containing 4% paraformaldehyde and fixed. The brain of the fixed mouse was extracted, fixed in phosphate buffered saline containing 4% paraformaldehyde for 24 hours to 48 hours, and treated with phosphate buffered saline containing 30% of sugar for about 24 hours. Then, the brain was placed in a mold for brain tissue, frozen on dry ice with an OCT composite containing 30% of a sugar solution, and kept at −80° C. before the brain was used. The mouse's frozen brain tissue was sliced at 40 µm using a cryostat microtome and then immunohistochemistry was performed.

When external damage is applied, mature astrocytes become radial glial cells through a reverse differentiation process. These types of cells express a progenitor cell marker named nestin and generate glial cells at a position thereof.

Figure 11:
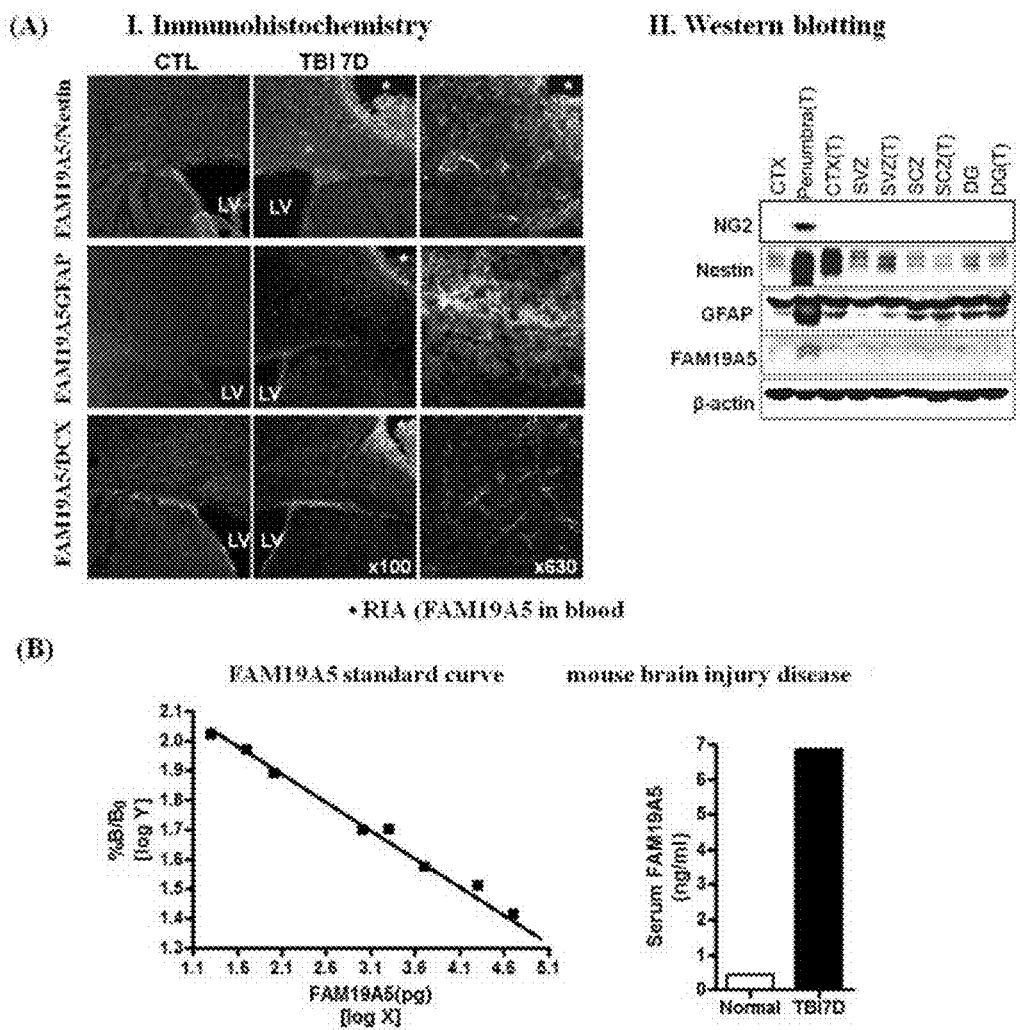
FIG. 11 shows the results obtained by measuring changes in FAM19A5 proteins in the traumatic brain injury model in mouse using immunohistochemistry (I) and Western blotting (II) (A), and in blood using radioimmunoassay (B).

As shown in FIG. 11A, a significant increase in the number of cells expressing FAM19A5 proteins was observed in a damaged region (penumbra). Radial glial cells in the damaged region express nestin serving as a marker and simultaneously express FAM19A5, and the amount of proteins significantly increased compared to a control group having no damage.

Also, although it is a very low ratio, neuroblasts migrated to the brain injury region from the subventricular zone through the corpus collosum (CC) did not express FAM19A5 peptides. In addition to the damaged region, in a periphery region of the subventricular zone in which a neural stem cell population is positioned, the number of cells expressing FAM19A5 proteins increased, and these simultaneously expressed GFAP serving as a marker of astrocytes. As a result, it was considered that FAM19A5 peptides generated from neural stem cells are more likely to be involved in generation of astrocytes than generation of neurons.

Meanwhile, a secretory factor of FAM19A5 is likely to be leaked into blood while the blood-brain barrier is damaged after brain injury. In this case, by determining expression or the degree of expression, a diagnosis marker capable of determining occurrence, progress, and alleviation of brain injury disease or brain disease may be developed. In order to know the possibility thereof, blood was obtained from normal mice and mice 7 days after brain injury, that were considered to have the highest expression of FAM19A5, and coagulated. Then, only serum was separated and a radioimmunoassay was performed.

The amount of proteins in serum was measured using a standard curve. As a result, surprisingly, 7 times or more FAM19A5 proteins were detected in the serum of the mice 7 days after brain injury compared to normal mice (FIG. 11B).

Example 11

Quantitative Change in FAM19A5 Proteins Over Time after Traumatic Brain Injury (TBI)

A quantitative change in FAM19A5 proteins over time after traumatic brain injury was observed in only reactive astrocytes expressing GFAP.

Figure 12:
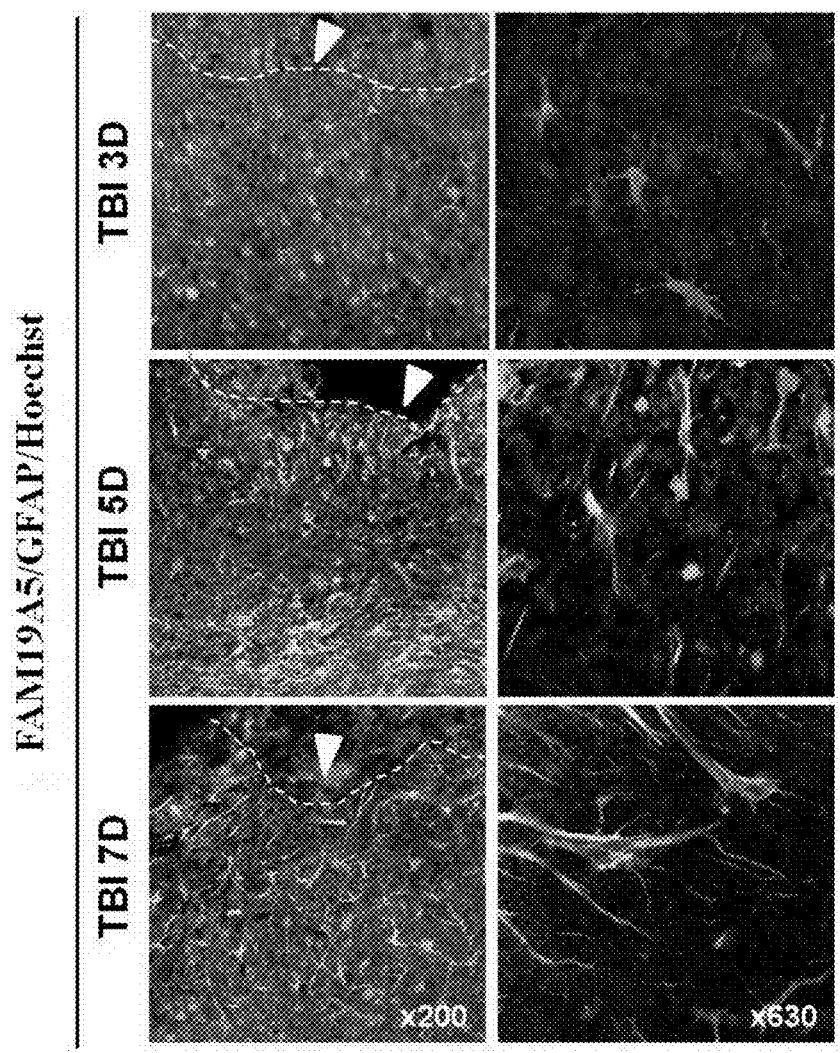
FIG. 12 shows the results obtained by measuring changes in FAM19A5 proteins over time after traumatic brain injury.

As shown in FIG. 12, it was determined that expression of FAM19A5 was relatively low in astrocytes labeled with GFAP 3 days after damage, expression started to increase after 5 days, and continuously increased for 7 days.

Example 12

Measurement of Quantitative Increase in FAM19A5 Proteins Shown in Amyotrophic Lateral Sclerosis (ALS)

In ALS model animal mSOD1 G93A Tg mice, immunostaining was performed on tissues in a period in which ALS symptoms were expressed. As shown in FIG. 13A, the results showed that expression of FAM19A5 increased to a very high level in the spinal cord of the mSOD1 G93A mouse compared to the same-aged mouse. Such an increase in expression was strongly observed in the ventral horn in which motor neurons particularly degenerated and died due to ALS are distributed. In this period, in the spinal cord of the mSOD1 G93A mouse, proliferation of glial cells was observed. Such a pathological modification process was also detected through GFAP double staining. Enlarged pictures on the bottom are high-magnification images of the ventral horn of the mSOD1 G93A mouse. It can be seen that most of the glial cells labeled with GFAP show a high level of FAM19A5 expression. Meanwhile, cells (indicated by an arrow) distributed at the center of the picture are considered as degenerative motor neurons since it had a circular nucleus and was not stained with GFAP. Even in this case, strong expression of FAM19A5 was observed. Nuclei were counter-labeled with blue fluorescence by Hoechst staining.

In addition, a change in expression was observed by immunoblotting. The result showed that expression of FAM19A5 increased to a very high level in the spinal cord of the ALS model mice (TG) compared to the wild-type (WT) mice (FIG. 13B).

A radioimmunoassay was performed in the same manner as in Example 10. The result showed that the amount of FAM19A5 proteins in the serum of the ALS model mice was detected at 3 times that of the normal mice or more (FIG. 13C).

Therefore, FAM19A5 detected in a brain injury model including traumatic brain injury and spinal cord damage disease models including amyotrophic lateral sclerosis may be developed as a labeling material of central nervous system damage.

Example 13

Delay Effect of Reactive Astrocytosis by FAM19A5 Antibody Treatment after Traumatic Brain Injury (TBI)

In order to determine a function of FAM19A5 proteins of which expression increased after brain injury is induced, FAM19A5 antibodies were injected into the vein of the mouse's tail one day after damage was induced. It was considered that, when traumatic brain injury is applied, the blood-brain barrier near the damaged region may be damaged and antibodies may be introduced into surrounding brain tissues.

Only when antibodies of FAM19A5 were injected, a fluorescence signal due to secondary antibodies was observed (FIG. 14).

Antibodies were injected one day after damage. After 3, 5, and 7 days had elapsed from the damage-inducing day, changes were observed using various cell markers.

Figure 15:
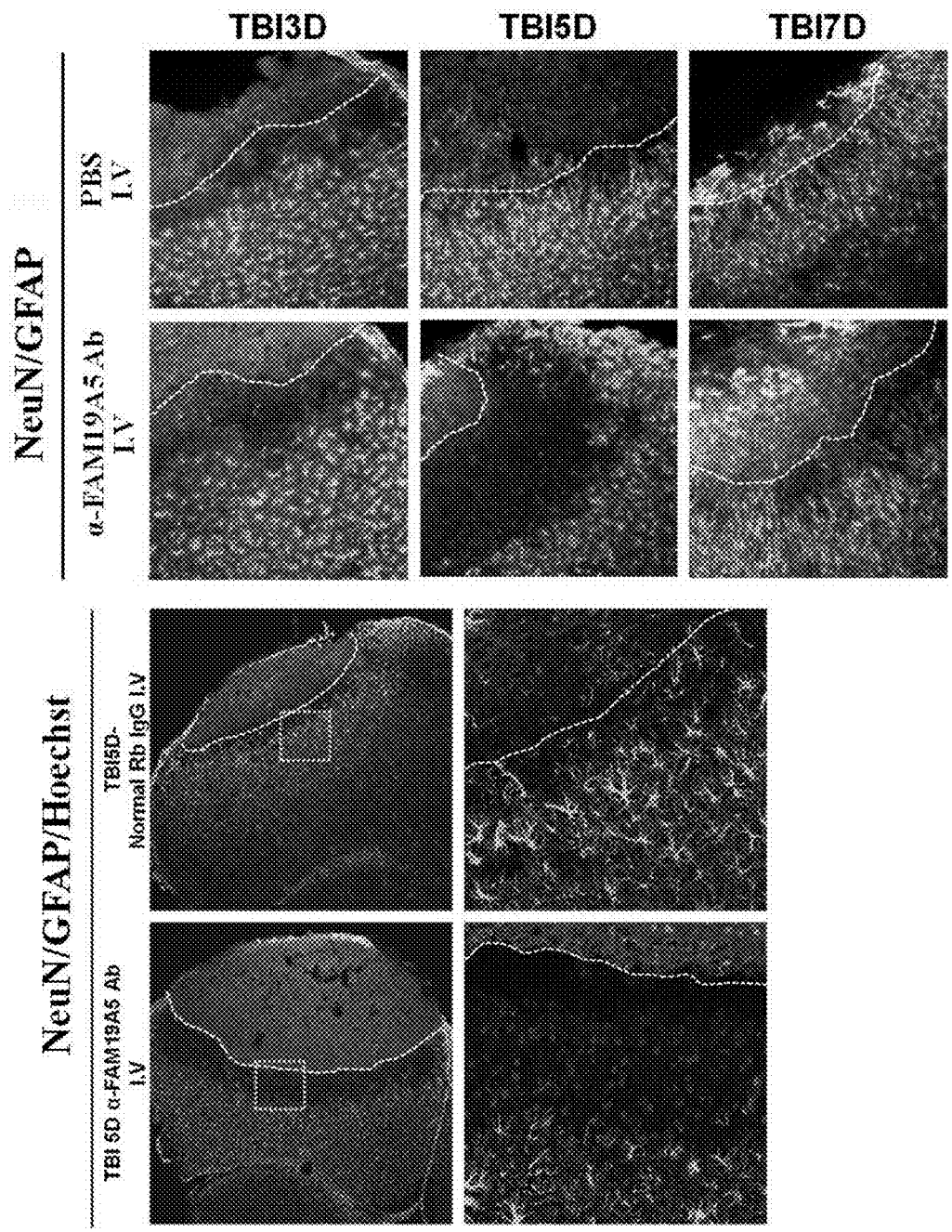
FIG. 15 shows changes in cell markers over time when treated with FAM19A5-specific antibodies after traumatic brain injury.

As shown in FIG. 15, in a mice model into which FAM19A5 antibodies were injected after 3 days had elapsed, generation of reactive astrocytes expressing GFAP was inhibited in the vicinity of damaged tissues, compared to a control group into which normal rabbit IgG was injected. Such a phenomenon was more significantly shown after 5 days had elapsed and weakly maintained even after 7 days had elapsed. Therefore, it is considered that inhibition of secreted FAM19A5 using antibodies influences surrounding cells, and particularly, delays reactive astrocytosis occurring after damage.

Meanwhile, reactive astrocytes generated after damage secrete a nerve growth factor that prevents programmed cell death such as GDNF and simultaneously resumes the uptake of glutamic acid, thereby positively acting to reduce the toxic environment around neurons. Therefore, in order to determine whether a delay in reactive astrocytosis according to FAM19A5 antibodies negatively influences a function for protecting neurons, TUNEL staining was performed.

Figure 16:
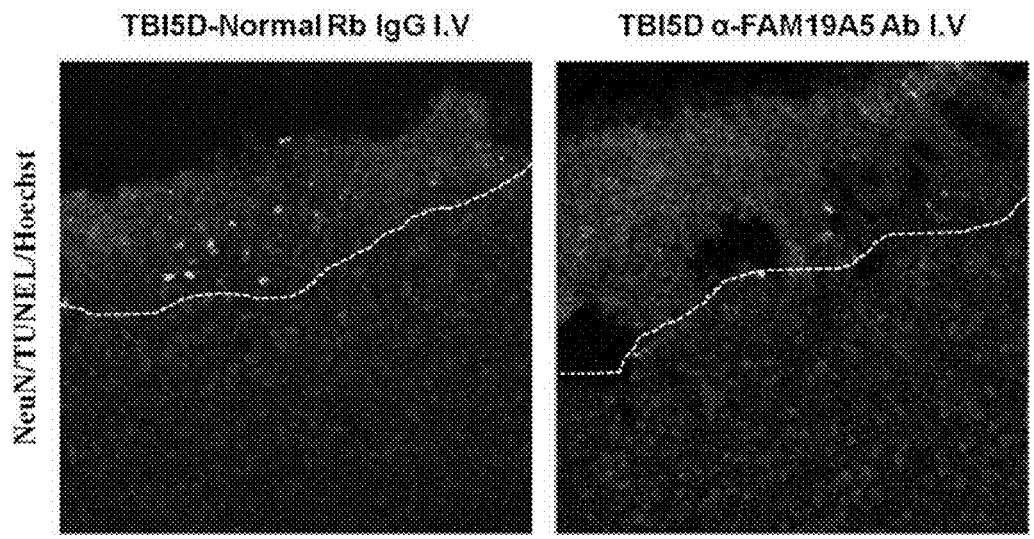
FIG. 16 shows changes in neurons when treated with FAM19A5-specific antibodies after traumatic brain injury.

As shown in FIG. 16, it was determined that cells expressing the neuron marker, NeuN, were not simultaneously stained with TUNEL, and a loss of reactive astrocytes does not kill neurons.

According to Example 10, reactive astrocytes generated from the damaged region after traumatic brain injury strongly expressed FAM19A5 proteins. Based on the result, in a mouse model treated with FAM19A5 antibodies after traumatic brain injury, positions of reactive astrocytes in which FAM19A5 proteins are expressed were determined.

Figure 17:
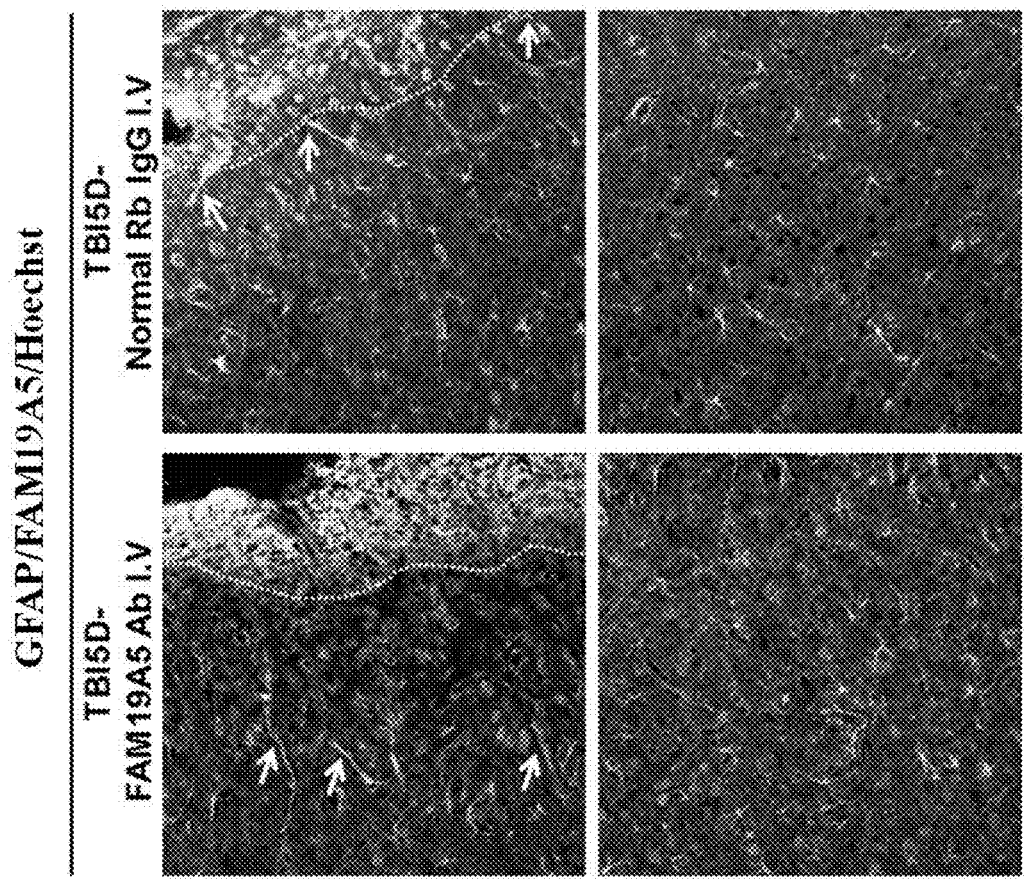
FIG. 17 shows the results obtained by determining positions of reactive astrocytes expressing FAM19A5 proteins in the traumatic brain injury model in mouse treated with FAM19A5-specific antibodies.

As expected, it was observed that astrocytes expressing FAM19A5 proteins were relatively separately positioned from the damaged region in the damage model into which FAM19A5 antibodies are injected, compared to a control group (FIG. 17).

Example 14

Numerical Decrease in NG2 Oligodendrocyte Progenitor Cells According to FAM19A5 Antibody Treatment after Traumatic Brain Injury (TBI)

Using the same experiment method described above, in order to determine whether FAM19A5 antibodies influence generation of other types of glial cells, staining was performed with several types of markers of glial cells.

Figure 18:
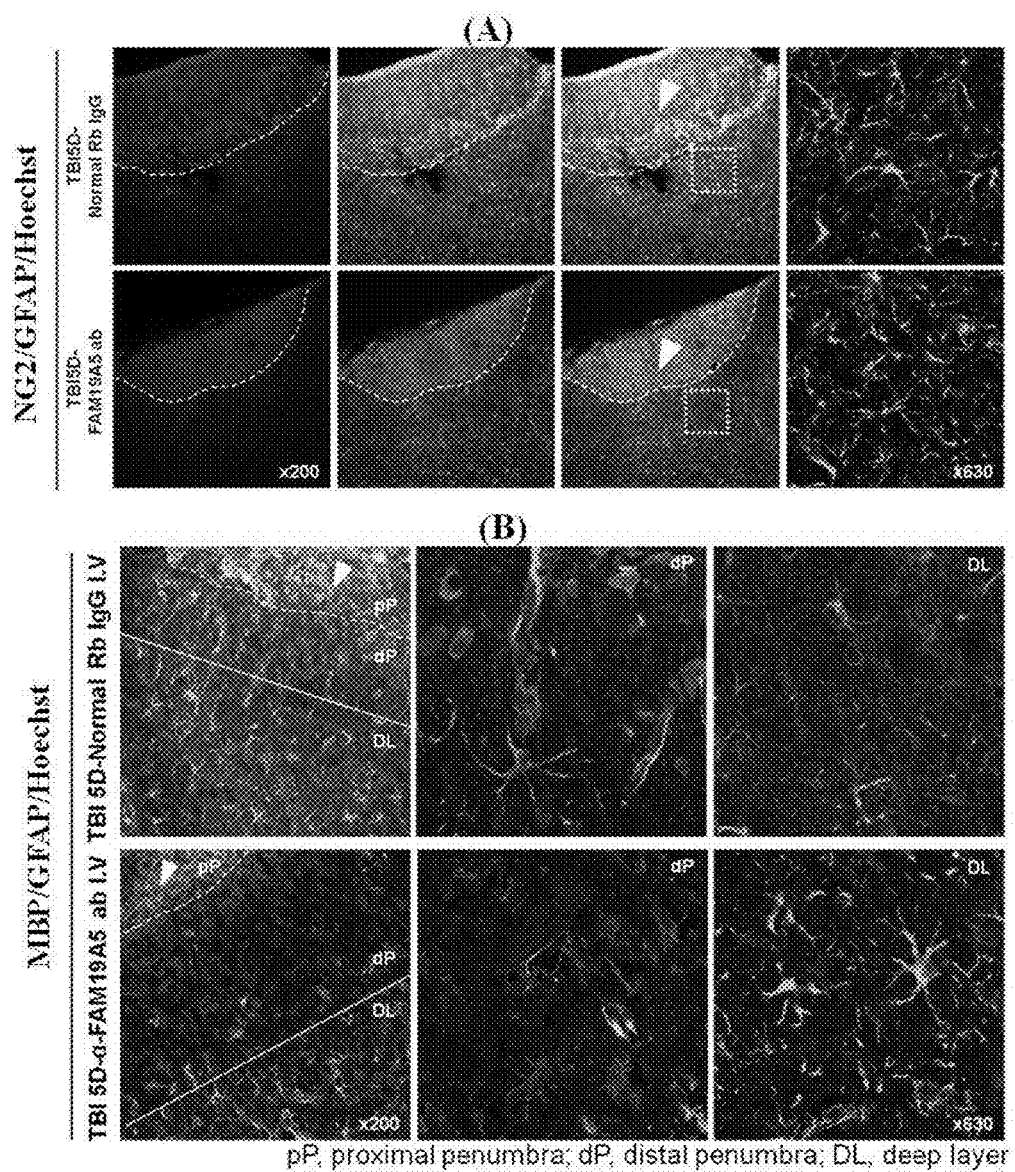
FIG. 18 shows the results obtained by measuring changes in NG2 oligodendrocyte progenitor cells (A) and oligodendrocyte cells (B) when treated with FAM19A5-specific antibodies after traumatic brain injury.

When 5 days had elapsed after brain injury, the number of oligodendrocyte progenitor cells expressing neuron-glial antigen 2 (NG2) decreased in the damaged region (FIG. 18A).

Meanwhile, since NG2 cells divided in damaged brain tissues are known to become oligodendrocytes that form a mature myelin sheath, mature oligodendrocytes labeled with a myelin basic protein (MBP) were observed and the number thereof also decreased (FIG. 18B).

Therefore, reactivation of FAM19A5 occurring after brain injury promotes proliferation of NG2 progenitor cells and is considered to be involved in myelinating axons of surrounding neurons.

The present invention has found that FAM19A5, which is a protein secreted from neural stem cells and regulates proliferation or differentiation of neural stem cells, is overexpressed in the event of cerebrospinal damage, promotes generation of astrocytes and recuperation of early damaged tissues, and when FAM19A5 is neutralized with antibodies specific to FAM19A5 in damaged tissues, generation of astrocytes is suppressed. Therefore, FAM19A5 may be used for diagnosis, prevention, or treatment of central nervous system damage, degenerative brain diseases, or central nervous system diseases.

FAM19A5 of the present invention or an inhibitor thereof may be used as a stem cell proliferation or differentiation regulator, and a diagnostic kit, a chip, or a therapeutic agent for central nervous system damage, degenerative brain disease, or central nervous system disease.

What is claimed is:

1. A method for delaying an onset of reactive gliosis in a subject in need thereof comprising administering to the subject an effective amount of an antibody or a fragment thereof that specifically binds to a family with sequence similarity 19 (FAM19A5) protein and is capable of delaying the onset of reactive gliosis within the subject.

2. The method of claim 1, wherein the subject suffers from a central nervous system damage or a degenerative brain disease associated with reactive gliosis.

3. The method of claim 2, wherein the central nervous system damage or the degenerative brain disease is further associated with a neuronal injury-induced increase of the number of oligodendrocyte progenitor cells expressing NG2 in the early stage of neuronal injury and/or a decrease in the TuJ positive neuron development.

4. The method of claim 2, wherein the central nervous system damage comprises a traumatic brain injury or a spinal cord damage.

5. The method of claim 2, wherein the degenerative brain disease comprises amyotrophic lateral sclerosis, Alzheimer's disease, Huntington's disease, or Parkinson's disease.

6. The method of claim 1, wherein the antibody or the fragment thereof promotes a myelination of an axon.

7. The method of claim 1, wherein the antibody or the fragment thereof promotes a survival of neurons.

8. The method of claim 1, wherein the antibody is a monoclonal antibody.

9. The method of claim 1, wherein the fragment thereof comprises a Fab, a Fab', a F(ab')2, a Fv fragment, a diabody, a linear antibody, a single chain antibody, or a multi-specific antibody formed from the antibody fragment.

10. The method of claim 1, wherein the antibody is a humanized antibody.

11. The method of claim 1, wherein the antibody is a human antibody.

12. The method of claim 1, wherein the antibody is a chimera antibody.

13. A method for attenuating a neuronal injury-induced increase of the number of oligodendrocyte progenitor cells expressing neuron-glial antigen 2 (NG2) in an early stage of neuronal injury in a subject in need thereof comprising administering to the subject an effective amount of an antibody or a fragment thereof that specifically binds to a FAM19A5 protein and is capable of attenuating a neuronal injury-induced increase of the number of oligodendrocyte progenitor cells expressing NG2 in the early stage of neuronal injury within the subject.

14. The method of claim 13, wherein the subject suffers from a central nervous system damage or a degenerative brain disease associated with a neuronal injury-induced increase of the number of oligodendrocyte progenitor cells expressing NG2 in the early stage of neuronal injury.

15. The method of claim 13, wherein the antibody is a humanized antibody.

16. The method of claim 13, wherein the antibody is a monoclonal antibody.

17. The method of claim 13, wherein the antibody is a human antibody.

18. The method of claim 13, wherein the fragment thereof comprises a Fab, a Fab', a F(ab')2, a Fv fragment, a diabody, a linear antibody, a single chain antibody, or a multi-specific antibody formed from the antibody fragment.

19. A method for increasing a TuJ positive neuron development in a subject in need thereof comprising administering to the subject an effective amount of an antibody or a fragment thereof that specifically binds to a FAM19A5 protein and is capable of increasing the TuJ positive neuron development within the subject.

20. The method of claim 19, wherein the subject suffers from a central nervous system damage or a degenerative brain disease associated with a decrease in the TuJ positive neuron development.

21. The method of claim 19, wherein the antibody is a humanized antibody.

22. The method of claim 19, wherein the antibody is a monoclonal antibody.

23. The method of claim 19, wherein the antibody is a human antibody.

24. The method of claim 19, wherein the fragment thereof comprises a Fab, a Fab', a F(ab')2, a Fv fragment, a diabody, a linear antibody, a single chain antibody, or a multi-specific antibody formed from the antibody fragment.

* * * * *

SEQUENCE LISTING

<160> NUMBER OF SEQ ID NOS: 20

<210> SEQ ID NO 1
<211> LENGTH: 18
<212> TYPE: DNA
<213> ORGANISM: Artificial Sequence
<220> FEATURE:
<223> OTHER INFORMATION: FAM19A1: forward primer

<400> SEQUENCE: 1
atggcaatgg tctctgca                                                 18

```
<210> SEQ ID NO 2
<211> LENGTH: 18
<212> TYPE: DNA
<213> ORGANISM: Artificial Sequence
<220> FEATURE:
<223> OTHER INFORMATION: FAM19A1: reverse primer

<400> SEQUENCE: 2
ttaggttctt gggtgaat                                                 18

<210> SEQ ID NO 3
<211> LENGTH: 18
<212> TYPE: DNA
<213> ORGANISM: Artificial Sequence
<220> FEATURE:
<223> OTHER INFORMATION: FAM19A2: forward primer

<400> SEQUENCE: 3
atgatcacca agatgaat                                                 18

<210> SEQ ID NO 4
<211> LENGTH: 20
<212> TYPE: DNA
<213> ORGANISM: Artificial Sequence
<220> FEATURE:
<223> OTHER INFORMATION: FAM19A2: reverse primer

<400> SEQUENCE: 4
ttaatgggtt accctagttg                                               20

<210> SEQ ID NO 5
<211> LENGTH: 18
<212> TYPE: DNA
<213> ORGANISM: Artificial Sequence
<220> FEATURE:
<223> OTHER INFORMATION: FAM19A3: forward primer

<400> SEQUENCE: 5
atggagaggc ccaccagc                                                 18

<210> SEQ ID NO 6
<211> LENGTH: 19
<212> TYPE: DNA
<213> ORGANISM: Artificial Sequence
<220> FEATURE:
<223> OTHER INFORMATION: FAM19A3: reverse primer

<400> SEQUENCE: 6
ttaccgtgtg accttggtg                                                19

<210> SEQ ID NO 7
<211> LENGTH: 19
<212> TYPE: DNA
<213> ORGANISM: Artificial Sequence
<220> FEATURE:
<223> OTHER INFORMATION: FAM19A4: forward primer

<400> SEQUENCE: 7
atgagagtct gtgctaagt                                                19

<210> SEQ ID NO 8
<211> LENGTH: 18
<212> TYPE: DNA
<213> ORGANISM: Artificial Sequence
<220> FEATURE:
<223> OTHER INFORMATION: FAM19A4: reverse primer
```

```
<400> SEQUENCE: 8
ctaccgggtc accttggt                                                    18

<210> SEQ ID NO 9
<211> LENGTH: 20
<212> TYPE: DNA
<213> ORGANISM: Artificial Sequence
<220> FEATURE:
<223> OTHER INFORMATION: FAM19A5: forward primer

<400> SEQUENCE: 9
atgcagctcc tgaaggcgct                                                  20

<210> SEQ ID NO 10
<211> LENGTH: 20
<212> TYPE: DNA
<213> ORGANISM: Artificial Sequence
<220> FEATURE:
<223> OTHER INFORMATION: FAM19A5: reverse primer

<400> SEQUENCE: 10
tcaggagacc gtggtggtct                                                  20

<210> SEQ ID NO 11
<211> LENGTH: 18
<212> TYPE: DNA
<213> ORGANISM: Artificial Sequence
<220> FEATURE:
<223> OTHER INFORMATION: FAM19A5: forward primer

<400> SEQUENCE: 11
atgcagctcc tgaaggcg                                                    18

<210> SEQ ID NO 12
<211> LENGTH: 18
<212> TYPE: DNA
<213> ORGANISM: Artificial Sequence
<220> FEATURE:
<223> OTHER INFORMATION: FAM19A5: reverse primer

<400> SEQUENCE: 12
tcaggagacc gtggtggt                                                    18

<210> SEQ ID NO 13
<211> LENGTH: 125
<212> TYPE: PRT
<213> ORGANISM: Homo sapiens

<400> SEQUENCE: 13
```

Met Gln Leu Leu Lys Ala Leu Trp Ala Leu Ala Gly Ala Ala Leu Cys
1               5                   10                  15

Cys Phe Leu Val Leu Val Ile His Ala Gln Phe Leu Lys Glu Gly Gln
            20                  25                  30

Leu Ala Ala Gly Thr Cys Glu Ile Val Thr Leu Asp Arg Asp Ser Ser
        35                  40                  45

Gln Pro Arg Arg Thr Ile Ala Arg Gln Thr Ala Arg Cys Ala Cys Arg
    50                  55                  60

Lys Gly Gln Ile Ala Gly Thr Thr Arg Ala Arg Pro Ala Cys Val Asp
65                  70                  75                  80

Ala Arg Ile Ile Lys Thr Lys Gln Trp Cys Asp Met Leu Pro Cys Leu
                85                  90                  95

```
Glu Gly Glu Gly Cys Asp Leu Leu Ile Asn Arg Ser Gly Trp Thr Cys
            100                 105                 110

Thr Gln Pro Gly Gly Arg Ile Lys Thr Thr Thr Val Ser
        115                 120                 125

<210> SEQ ID NO 14
<211> LENGTH: 132
<212> TYPE: PRT
<213> ORGANISM: Mus musculus

<400> SEQUENCE: 14

Met Ala Pro Ser Pro Arg Thr Ser Ser Arg Gln Asp Ala Thr Ala Leu
1               5                   10                  15

Pro Ser Met Ser Ser Thr Phe Trp Ala Phe Met Ile Leu Ala Ser Leu
            20                  25                  30

Leu Ile Ala Tyr Cys Ser Gln Leu Ala Ala Gly Thr Cys Glu Ile Val
        35                  40                  45

Thr Leu Asp Arg Asp Ser Ser Gln Pro Arg Arg Thr Ile Ala Arg Gln
    50                  55                  60

Thr Ala Arg Cys Ala Cys Arg Lys Gly Gln Ile Ala Gly Thr Thr Arg
65                  70                  75                  80

Ala Arg Pro Ala Cys Val Asp Ala Arg Ile Ile Lys Thr Lys Gln Trp
                85                  90                  95

Cys Asp Met Leu Pro Cys Leu Glu Gly Glu Gly Cys Asp Leu Leu Ile
            100                 105                 110

Asn Arg Ser Gly Trp Thr Cys Thr Gln Pro Gly Gly Arg Ile Lys Thr
        115                 120                 125

Thr Thr Val Ser
        130

<210> SEQ ID NO 15
<211> LENGTH: 132
<212> TYPE: PRT
<213> ORGANISM: Rattus norvegicus

<400> SEQUENCE: 15

Met Ala Pro Ser Pro Arg Thr Ser Ser Arg Gln Asp Ala Thr Ala Leu
1               5                   10                  15

Pro Ser Met Ser Ser Thr Phe Trp Ala Phe Met Ile Leu Ala Ser Leu
            20                  25                  30

Leu Ile Ala Tyr Cys Ser Gln Leu Ala Ala Gly Thr Cys Glu Ile Val
        35                  40                  45

Thr Leu Asp Arg Asp Ser Ser Gln Pro Arg Arg Thr Ile Ala Arg Gln
    50                  55                  60

Thr Ala Arg Cys Ala Cys Arg Lys Gly Gln Ile Ala Gly Thr Thr Arg
65                  70                  75                  80

Ala Arg Pro Ala Cys Val Asp Ala Arg Ile Ile Lys Thr Lys Gln Trp
                85                  90                  95

Cys Asp Met Leu Pro Cys Leu Glu Gly Glu Gly Cys Asp Leu Leu Ile
            100                 105                 110

Asn Arg Ser Gly Trp Thr Cys Thr Gln Pro Gly Gly Arg Ile Lys Thr
        115                 120                 125

Thr Thr Val Ser
        130

<210> SEQ ID NO 16
<211> LENGTH: 111
```

```
<212> TYPE: PRT
<213> ORGANISM: Gallus gallus

<400> SEQUENCE: 16

Met Ser Ser Gln Phe Cys Tyr Ile His Gln Leu Ala Ala Ile Tyr Cys
1               5                   10                  15

Gly Gln Leu Ala Ala Gly Thr Cys Glu Ile Val Thr Leu Asp Arg Asp
            20                  25                  30

Ser Ser Gln Pro Arg Arg Thr Ile Ala Arg Gln Thr Ala Arg Cys Ala
        35                  40                  45

Cys Lys Lys Gly Gln Ile Ala Gly Thr Thr Arg Ala Arg Pro Ala Cys
    50                  55                  60

Val Asp Gly Lys Phe Met Pro Ile Gln Glu Trp Cys Gln Leu Val Ala
65                  70                  75                  80

Cys Leu Glu Gly Glu Gly Cys Asp Leu Leu Ile Asn Lys Ser Gly Trp
                85                  90                  95

Thr Cys Thr Gln Pro Gly Gly Arg Ile Lys Thr Thr Thr Val Asn
            100                 105                 110

<210> SEQ ID NO 17
<211> LENGTH: 125
<212> TYPE: PRT
<213> ORGANISM: Taeniopygia guttata

<400> SEQUENCE: 17

Met Gln Leu Leu Lys Ala Leu Trp Ala Leu Ala Gly Ala Ala Ile Cys
1               5                   10                  15

Cys Phe Leu Ile Phe Val Ile His Ser Gln Phe Leu Lys Glu Gly Gln
            20                  25                  30

Leu Ala Ala Gly Thr Cys Glu Ile Val Thr Leu Asp Arg Asp Ser Ser
        35                  40                  45

Gln Pro Arg Arg Thr Ile Ala Arg Gln Thr Ala Arg Cys Ala Cys Lys
    50                  55                  60

Lys Gly Gln Ile Ala Gly Thr Thr Arg Ala Arg Pro Ala Cys Val Asp
65                  70                  75                  80

Ala Arg Ile Ile Lys Thr Lys Gln Trp Cys Glu Met Leu Pro Cys Leu
                85                  90                  95

Glu Gly Glu Gly Cys Asp Leu Leu Ile Asn Lys Ser Gly Trp Thr Cys
            100                 105                 110

Thr Gln Pro Gly Gly Arg Ile Lys Thr Thr Thr Val Gly
            115                 120                 125

<210> SEQ ID NO 18
<211> LENGTH: 125
<212> TYPE: PRT
<213> ORGANISM: Xenopus laevis

<400> SEQUENCE: 18

Met Gln Leu Leu Lys Ala Leu Trp Ala Leu Ala Gly Ala Ala Ile Cys
1               5                   10                  15

Cys Phe Leu Leu Phe Leu Ile His Ser Gln Phe Leu Lys Glu Gly Gln
            20                  25                  30

Leu Ala Ala Gly Thr Cys Glu Val Val Thr Tyr Asp Arg Asp Ser Ser
        35                  40                  45

Gln Pro Arg Arg Thr Ile Ala Arg Gln Thr Ala Arg Cys Ala Cys Lys
    50                  55                  60

Lys Gly Gln Ile Ala Gly Thr Thr Arg Ala Lys Pro Ala Cys Val Asp
```

```
            65                  70                  75                  80
Ala Arg Ile Ile Lys Thr Lys Gln Trp Cys Glu Met Leu Pro Cys Leu
                    85                  90                  95
Glu Gly Glu Gly Cys Glu Leu Leu Asn Lys Ser Gly Trp Thr Cys
                100                 105                 110
Met Gln Pro Gly Gly Arg Ile Lys Thr Thr Val Met
            115                 120                 125

<210> SEQ ID NO 19
<211> LENGTH: 131
<212> TYPE: PRT
<213> ORGANISM: Danio rerio

<400> SEQUENCE: 19

Met Leu Lys Ala Val Arg Met Leu Met Leu Arg Val Ala Trp Ala Leu
1               5                   10                  15
Ala Gly Ala Ala Val Cys Cys Phe Leu Ile Val Leu Ile His Ser Arg
                20                  25                  30
Phe Leu Arg Asp Gly Gln Leu Ala Ala Gly Thr Cys Glu Ile Val Thr
            35                  40                  45
Leu Asp Lys Asp Ser Ser Gln Pro Arg Arg Thr Ile Ala Arg Gln Thr
    50                  55                  60
Ala Arg Cys Ala Cys Lys Lys Gly Gln Ile Ala Gly Thr Thr Asn Ala
65                  70                  75                  80
Arg Pro Ala Cys Val Asp Ala Arg Ile Val Lys Thr Lys Gln Trp Cys
                85                  90                  95
Asp Met Val Pro Cys Leu Glu Asp Glu Cys Asp Leu Leu Val Asn
                100                 105                 110
Lys Ser Gly Trp Thr Cys Thr Gln Pro Ser Gly Arg Val Lys Thr Thr
            115                 120                 125
Thr Val Ser
    130

<210> SEQ ID NO 20
<211> LENGTH: 125
<212> TYPE: PRT
<213> ORGANISM: Gasterosteus aculeatus aculeatus

<400> SEQUENCE: 20

Met Gln Leu Leu Arg Leu Ala Trp Ala Val Thr Ala Ser Ala Val Cys
1               5                   10                  15
Phe Leu Leu Leu Ile Leu His Asn Gln Val Leu Arg Glu Gly Gln
                20                  25                  30
Leu Ala Ala Gly Thr Cys Glu Ile Val Thr Leu Asp Arg Asp Ser Ser
            35                  40                  45
Gln Pro Arg Arg Thr Ile Ala Arg Gln Thr Ala Arg Cys Ala Cys Arg
    50                  55                  60
Lys Gly Arg Ile Ala Gly Thr Thr Arg Ala Pro Ala Cys Val Asp
65                  70                  75                  80
Gly Arg Ile Val Trp Thr Arg Gln Trp Cys Glu Met Ser Pro Cys Leu
                85                  90                  95
Asp Asp Glu Gly Cys Asp Leu Leu Val Asn Gln Ser Gly Trp Thr Cys
                100                 105                 110
Thr Gln Pro Gly Gly Arg Val Lys Thr Thr Val Ser
            115                 120                 125
```